(12) United States Patent
Esko

(10) Patent No.: US 7,772,192 B2
(45) Date of Patent: Aug. 10, 2010

(54) COMPOSITIONS AND METHODS FOR TREATMENT OF DISEASE WITH ACETYLATED DISACCHARIDES

(75) Inventor: Jeffrey D. Esko, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 897 days.

(21) Appl. No.: 10/559,260

(22) PCT Filed: Jun. 1, 2004

(86) PCT No.: PCT/US2004/017512

§ 371 (c)(1),
(2), (4) Date: Jul. 26, 2006

(87) PCT Pub. No.: WO2005/000860

PCT Pub. Date: Jan. 6, 2005

(65) Prior Publication Data

US 2007/0161598 A1    Jul. 12, 2007

Related U.S. Application Data

(60) Provisional application No. 60/475,306, filed on Jun. 3, 2003.

(51) Int. Cl.
*A61K 31/7028* (2006.01)
*A61K 31/7034* (2006.01)
*A61K 31/704* (2006.01)
*A61K 31/7024* (2006.01)
*C07H 15/18* (2006.01)
*C07H 15/20* (2006.01)
*C07H 15/203* (2006.01)
*C07H 15/256* (2006.01)
*C07H 15/04* (2006.01)

(52) U.S. Cl. ............................. 514/25; 514/33; 514/34; 514/42; 536/18.1; 536/4.1; 536/29.1

(58) Field of Classification Search ........................ None
See application file for complete search history.

(56) References Cited

U.S. PATENT DOCUMENTS 5,639,734 A    6/1997    Esko et al.

FOREIGN PATENT DOCUMENTS

WO    WO2005/037293    * 4/2005

OTHER PUBLICATIONS

The Oxford Textbook of Oncology, 1995, published by Oxford University Press, pp. 447-453.*
The Merck Manual of Diagnosis and Therapy, seventeenth edition, 1999, Published by Merck Research Laboratories, pp. 397-398, 948-949, 1916, and 1979-1981.*
Furuhata et al., "Reaction of Glycosyl Halides with 7-Hydroxy-9a-methoxymitosane Sodium Salt" Chem Pharm Bull (1989) vol. 37 No. 10, pp. 2651-2654.*
Pinkel, Donald The Use of Body Surface Area as a Criterion of Drug Dosage in Cancer Chemotherapy* Cancer Research (1958) vol. 18, pp. 853-856.*
Kwon et al., "A Phase II Study of Vinorelbine, Mitomycin C and Cisplatin Chemotherapy for Advanced Non-Small Cell Lung Cancer" The Korean Journal of Internal Medicine (2002) vol. 17 No. 4, pp. 240-244.*
Baird, A., et al., "Receptor- and heparin-binding domains of basic fibroblast growth factor", *Proc. Natl. Acad. Scie. USA*, Apr. 1988, pp. 2324-2328, vol. 85, Medical Sciences.
Brown, J.R., et al., "Expression Patterns of α2,3-Sialyltransferases and α1,3-Fucosyltransferases Determine the Mode of Sialyl Lewis X Inhibition by Disaccharide Decoys", *Jour. Biol. Chemi.*, Jun. 27, 2003, pp. 23352-23359, vol. 278, No. 26.
Fuster, M.M., et al., "A Disaccharide Precursor of Sialyl Lewis X Inhibits Metastatic Potential of Tumor Cells", *Cancer Research*, Jun. 1, 2003, pp. 2775-2781, vol. 63.
Sarkar, A.K., et al., "Disaccharide uptake and priming in animal cells: Inhibition of sialyl Lewis X by acetylated Galβ1→4GlcnAcβ-O-naphthalenemethanol", *Proc, Natl. Acad. Sci. USA*, Apr. 1995, pp. 3323-3327, vol. 92, Biochemistry.
Sarkar, A.K., et al., "Fucosylation of Disaccharide Precursors of Sialyl Lewis$^x$ Inhibit Selectin-mediated Cell Adhesion", *Jour. Biol. Chemi.*, Oct. 10, 1997, pp. 25608-25616, vol. 272, No. 41.
Sarkar, A.K., et al., "Synthesis and glycan priming activity of acetylated disaccharides", *Carbohydrate Res.*, 2000, pp. 287-300, vol. 329.
Kojima, N. et al, "Inhibition of selectin-dependent tumor cell adhesion to endothelial cells and platelets by blocking O-glycosylation of these cells", *Biochem.Biophys.Res.Comm.*, 1992, pp. 1288-1295, vol. 18, (Abstract only).

* cited by examiner

*Primary Examiner*—Eric S Olson
(74) *Attorney, Agent, or Firm*—Procopio, Cory, Hargreaves & Savitch, LLP

(57) ABSTRACT

Compositions and methods for treatment of disease with acetylated disaccharides and analogs thereof are provided.

33 Claims, 16 Drawing Sheets

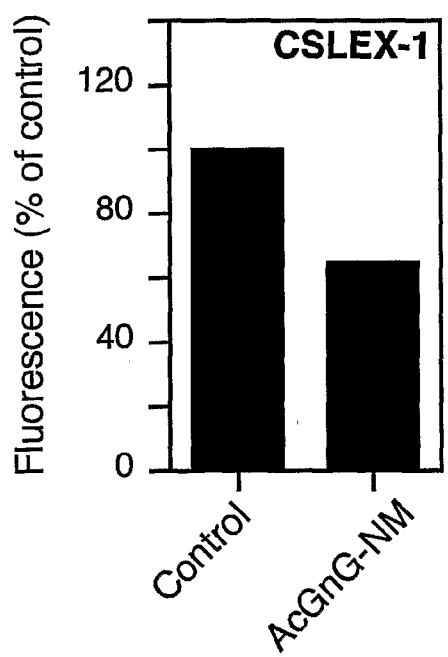 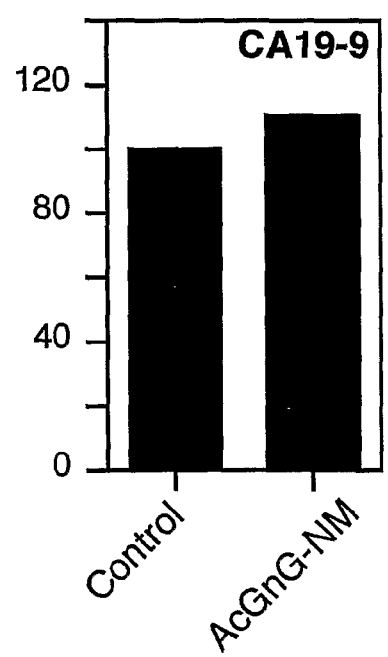
FIG. 2A  FIG. 2B

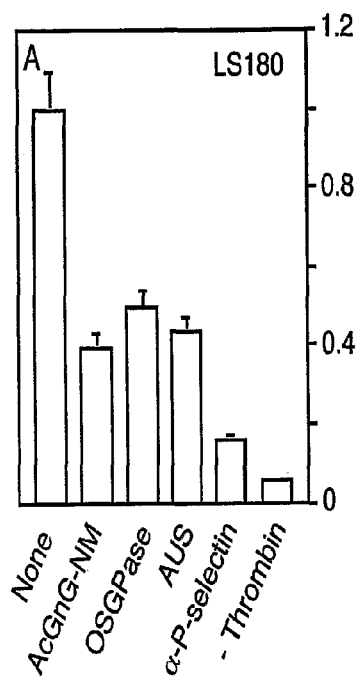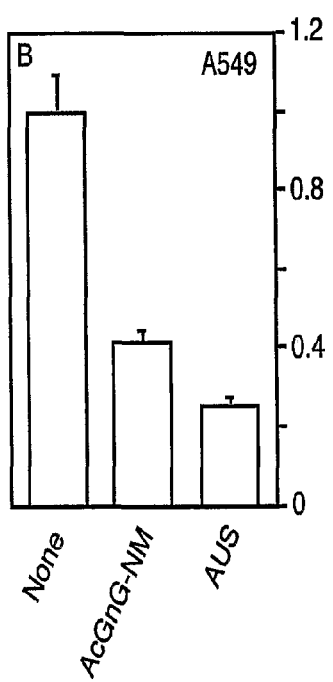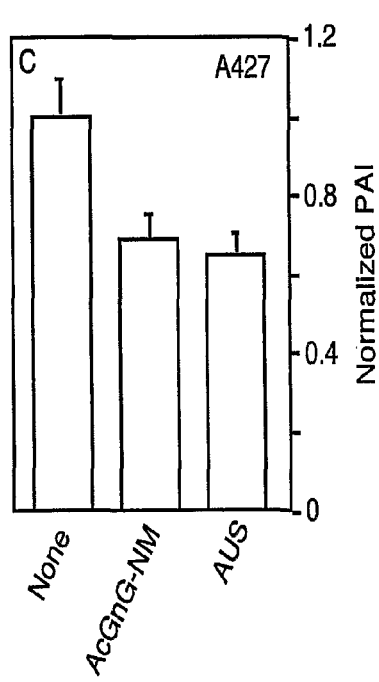
FIG. 5A  FIG. 5B  FIG. 5C

AcGnG-NM

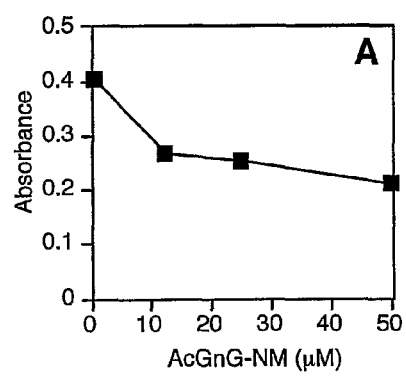
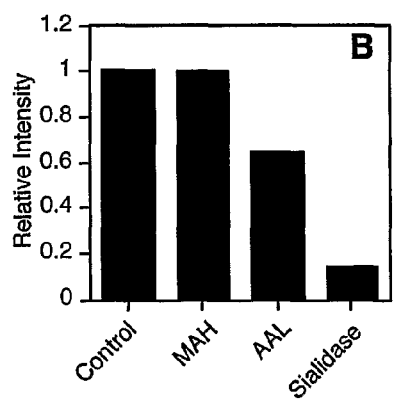
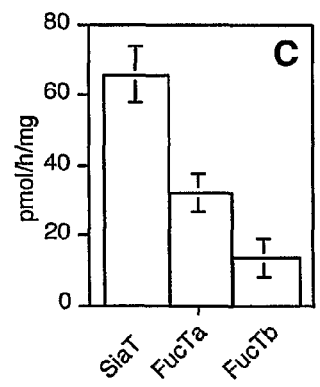
FIG. 10A  FIG. 10B  FIG. 10C

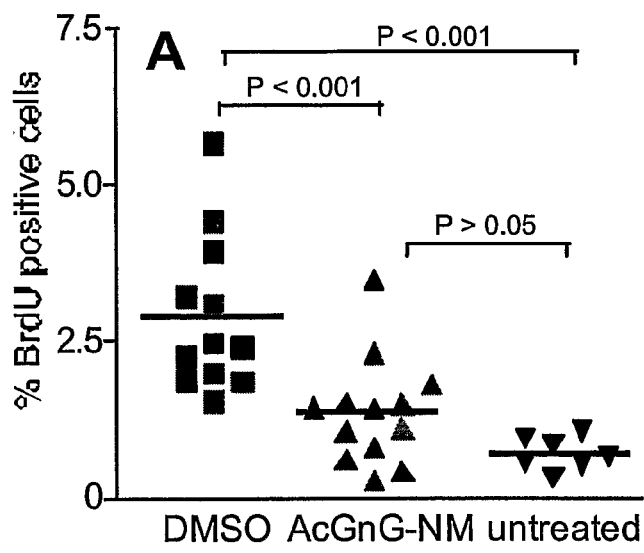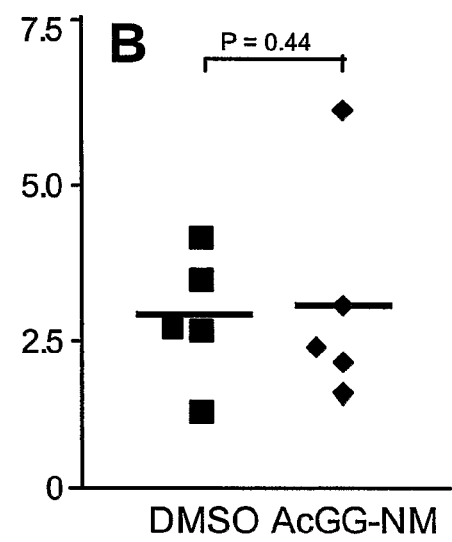
FIG. 13A   FIG. 13B

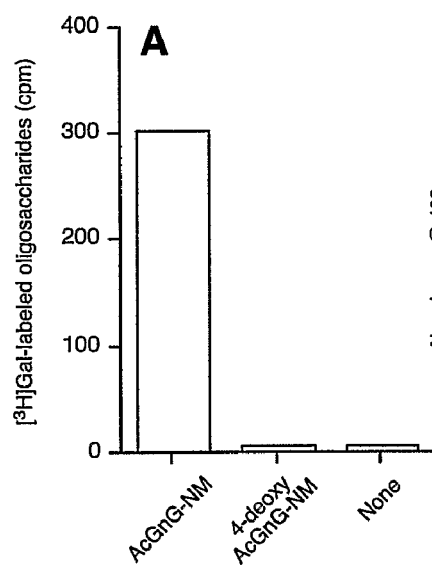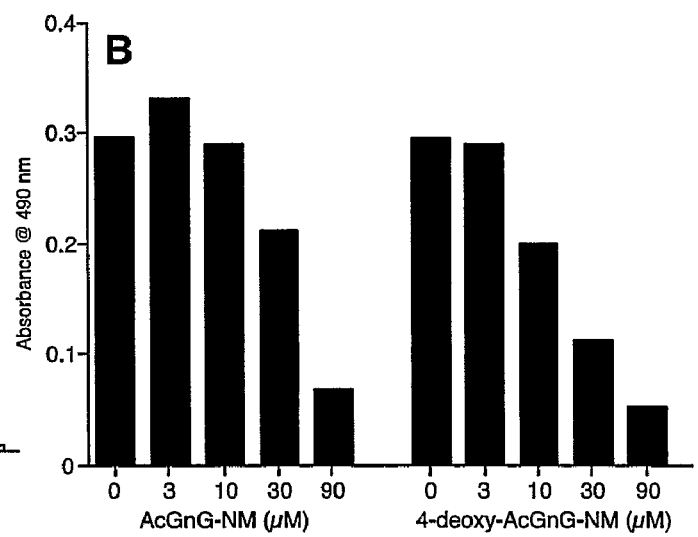
FIG. 15A FIG. 15B

COMPOSITIONS AND METHODS FOR TREATMENT OF DISEASE WITH ACETYLATED DISACCHARIDES

This application is a national stage application of PCT international application PCT/US04/17512, filed Jun. 1, 2004, which claims benefit of provisional application No. 60/475,306, filed Jun. 3, 2003.

This research was supported by National Institutes of Health Grant CA46462. The government may have certain rights in this invention.

FIELD

The invention generally relates to compositions and methods for treatment of disease with acetylated disaccharides and analogs thereof.

BACKGROUND

Tumor metastasis is thought to depend on cell adhesion between blood-borne tumor cells, circulating platelets (facilitating platelet-tumor emboli), and endothelia, promoting arrest in the vasculature, growth, and extravasation. Tang et al., *Invasion Metastasis*, 14: 109-122, 1994; McEver et al., *Glycoconjugate J.*, 14: 585-591, 1997; Krause et al., *Clin. Exp. Metastasis*, 17: 183-192, 1999. Several types of adhesion receptors and ligands have been described as important elements in this process, including selecting, chemokines and integrins. Tang et al., *Invasion Metastasis*, 14: 109-122, 1994; Kannagi, *Glycoconjugate J.*, 14: 577-584, 1997; Behrens, *Breast Cancer Res. Treat.*, 24: 175-184., 1993. Overall, these features of tumor cell adhesion resemble characteristics of leukocyte extravasation during inflammation. In both cases, expression of the oligosaccharides, sialyl Lewis X [sLe$^X$-Sia$\alpha$2,3Gal$\beta$1, 4(Fuc$\alpha$1,3)GlcNAc] and sialyl Lewis a[sLe$^a$-Sia$\alpha$2,3Gal$\beta$1,3(Fuc$\alpha$1,4)GlcNAc] on cell-surface glycoconjugates endows cells with the ability to adhere to E-, P-, and L-selectins present on endothelia, platelets, or leukocytes. Studies of human tumors and mice bearing genetic alterations in one or more selectins underscore the importance of these interactions in hematogenous spread of cancer cells. Biancone et al., *J. Exp. Med.*, 183: 581-587, 1996; Renkonen et al., *Int. J. Cancer*, 74: 296-300, 1997; Frenette et al., *Thromb Haemost*, 78: 60-64, 1997; Kim et al., *Proc. Natl. Acad. Sci. USA*, 95: 9325-9330, 1998; Borsig et al., *Proc. Natl. Acad. Sci. USA*, 98: 3352-3357, 2001.

The carbohydrate ligands for the selectins are predominantly O-linked glycoprotein mucins and glycolipids that display sLe$^X$ or sLe$^a$ in clustered arrangements. Fukuda, *Cancer Res.*, 56: 2237-2244, 1996; Kansas, *Blood*, 88: 3259-3287, 1996; Kim et al., *Am. J. Pathol.*, 155: 461-472, 1999. Several aggressive solid tumors display significant reactivity to anti-sLe$^X$ monoclonal antibodies and E- and P-selectins. These include a relatively large proportion of tumors from the lung, colon, and breast. Kannagi, *Glycoconjugate J.*, 14: 577-584, 1997; Renkonen et al., *Int. J. Cancer*, 74: 296-300, 1997; Kim et al., *Am. J. Pathol.*, 155: 461-472, 1999; Fukushima et al., *Cancer Res.*, 44: 5279-5285, 1984; Kannagi et al., *Cancer Res.*, 46: 2619-2626, 1986; Mannori et al., *Cancer Res.*, 55: 4425-4431, 1995; Nakamori et al., *J. Clin. Oncol.*, 15: 816-825, 1997. Adhesion interactions involving sLe$^X$ constitute important early steps in the pathophysiology of metastasis possibly by stabilizing "neoplastic emboli" via P-selectins on platelets or L-selectin on leukocytes, or by facilitating adhesion to and possible extravasation thorough the endothelium. Kim et al., *Proc. Natl. Acad. Sci. USA*, 95: 9325-9330, 1998; Borsig et al., *Proc. Natl. Acad. Sci. USA*, 98: 3352-3357, 2001; Rice et al., *Science*, 246: 1303-1306, 1989; Stone et al., *J. Clin. Invest.*, 92: 804-813, 1993; Honn et al., *Cancer Metastasis Rev.*, 11: 325-351, 1992; Frenette et al., *J. Exp. Med.*, 191: 1413-1422, 2000. The importance of these interactions derives from studies in patients post-resection from colon, lung, gastric, and other carcinomas that show that survival correlates inversely with tumor expression of sLe$^X$. Ogawa et al., *J. Thorac. Cardiovasc. Surg.*, 108: 329-336, 1994; Nakamori et al., *Dis. Colon Rectum*, 40: 420-431, 1997; Baldus et al., *Tumour Biol.*, 19: 445-453, 1998.

Research has focused on the development of small molecule inhibitors that might block the expression of Lewis carbohydrate antigens on cells. Per-O-acetylated disaccharides (acetylated forms of Gal$\beta$1,4GlcNAc$\beta$-O-naphthalenemethanol [AcGGn-NM] or GlcNAc$\beta$1,3Gal$\beta$-O-naphthalenemethanol [AcGnG-NM]) are taken up by cells, deacetylated, and acted on as substrates by relevant glycosyltransferases located in the Golgi. Assembly of oligosaccharides on the disaccharides takes place, resulting in diversion of glycan biosynthesis from endogenous glycoconjugates. Sarkar et al., *Proc. Natl. Acad. Sci. USA*, 92: 3323-3327, 1995; Sarkar et al., *J. Biol. Chem.*, 272: 25608-25616, 1997; Sarkar et al., *Carbohydr. Res.*, 329: 287-300, 2000. The result is a concomitant reduction of sLe$^X$ expression on the cell surface. The monosaccharide, GalNAc$\alpha$-O-benzyl, behaves in a similar fashion, altering the expression of O-linked chains on mucins of colon and leukemia cell lines in vitro and altering cell adhesion to platelets and endothelia Niv et al., *Int. J. Cancer*, 50: 147-152, 1992; Kojima et al., *Biochem. Biophys. Res. Commun.*, 182: 1288-1295, 1992; Delannoy et al., *Glycoconjugate J.*, 13: 717-726, 1996. However, much higher concentrations of the monosaccharide are needed to achieve a similar level of inhibition as the disaccharide (1-5 mM versus 10-50 µM, respectively). Fuster et al., *Cancer Research* 63: 2775-2781, 2003; Sarkar et al., *Proc. Natl. Acad. Sci.* 92: 3323-3327, 1994; Hindsgaul et al., *J. Biol. Chem.* 266:17858-17862, 1991; Khan et al., *J. Biol. Chem.* 268: 2468-2473, 1993; Lowary et al., *Carbohydr. Res.* 251:33-67, 1994; Linker et al., *Carbohydr. Res.* 245: 323-331, 1993. A need exists in the art for more potent inhibitors that block the expression of Lewis carbohydrate antigens on cells and can act as a therapeutic agent to control or prevent tumor metastasis.

SUMMARY

The invention generally relates to compounds and methods for treatment or prevention of neoplastic disease or metastatic disease. The compounds and methods for treatment of the present invention utilize a class of chemotherapeutic agents comprising acetylated disaccharides. Benefits of the present invention include the ability of a class of disaccharides, per-O-acetylated disaccharides, for example, acetylated forms of GlcNAc$\beta$1,3Gal$\beta$-O-naphthalenemethanol (AcGnG-NM), to inhibit adhesion of adenocarcinoma cells to both immobilized recombinant selectins as well as selectins on activated human platelets and endothelia. The results demonstrate that inhibiting tumor cell glycosylation in this way leads to decreased interactions with selecting, increased susceptibility to leukocyte-mediated lysis, and reduction in organ colonization in experimental models of metastasis.

In an embodiment of the invention, compounds and methods for treatment demonstrate an ability to reduce tumor cells aggregation in lung tissue and to form tumors in a mouse model for tumor metastasis. The invention further provides a therapeutic composition for administration of a therapeutic dose of the acetylated disaccharide of the invention for the treatment of neoplastic disease and the prevention or reduction of tumor metastasis.

In one embodiment, a disaccharide inhibitor of glycosyltransferase comprises the structure, sugar-X-sugar-Y—R, wherein the sugars are glucose, galactose, N-acetylglucosamine, glucosamine, N-acetylgalactosamine, galactosamine, sialic acid, fucose or mannose; X is a bridging atom, O, C, S, or N, and wherein X is a 1-2, 1-3, 1-4, or 1-6 linkage with anomeric configuration, α or β, between the sugars; Y is a bridging atom, O, C, S, or N, with anomeric configuration, α or β; R is an aglycone, benzyl, phenyl, naphthol, naphthalenemethanol, indenol, a heterocyclic derivative of indenol, a heterocyclic derivative of naphthol, a heterocyclic derivative of naphthalenemethanol, an alkyl group of 1-16 carbons, or a polyisoprenoid; and wherein, independently, the sugar is O-alkyl, O-acyl, or O-aryl substituted for a hydroxyl group; the sugar is alkyl-, aryl-, epoxy-, amid-, thiol- or halo-substituted for a hydroxyl group; or the sugar is S-alkyl, N-alkyl, S-acyl, N-acyl, C-acyl, S-aryl, or N-aryl substituted for a hydroxyl group. In a detailed embodiment, the disease is neoplastic disease, metastatic disease inflammation, wound healing, lysosomal storage diseases, atherosclerosis, or diabetes.

In a further detailed embodiment, the disaccharide is per-O-acetylated Galβ1,4GlcNAc-Y—R, per-O-acetylated Galβ1,3GlcNAc-Y—R, per-O-acetylated Galβ1,3GalNAc-Y—R, per-O-acetylated GlcNAcβ1,3Gal-Y—R, per-O-acetylated GlcNAcβ1,3GalNAc-Y—R, per-O-acetylated GlcNAcβ1,6GalNAc-Y—R, or per-O-acetylated GlcNAcβ1,4GlcNAc-Y—R, wherein R is an aglycone, benzyl, phenyl, naphthol, naphthalenemethanol, indenol, a heterocyclic derivative of indenol, a heterocyclic derivative of naphthol, a heterocyclic derivative of naphthalenemethanol, an alkyl group of 1-16 carbons, or a polyisoprenoid; Y is an oxygen atom. In a further detailed embodiment, the disaccharide is per-O-acetylated Galβ1,4GlcNAc-O-2-naphthalenemethanol (NM), per-O-acetylated GlcNAcβ1,3Gal-O-NM, per-O-acetylated GlcNAcβ1,3 Gal-O-Bn, per-O-acetylated GlcNAcβ1,3Gal-O-Ph, per-O-acetylated GlcNAcβ1,3Gal-O-2-naphthol, per-O-acetylated Galβ1,3GalNAc-O-NM, per-O-acetylated GlcNAcβ1,3GalNAc-O-NM, per-O-acetylated GlcNAcβ1,6GalNAc-O-NM, per-O-acetylated 3-deoxy-GlcNAcβ1,3Gal-O-NM, per-O-acetylated 4-deoxy-GlcNAcβ1,3Gal-O-NM, per-O-acetylated 3-fluoro-GlcNAcβ1,3Gal-O-NM, per-O-acetylated 4-fluoro-GlcNAcβ1,3Gal-O-NM, per-O-acetylated Galβ1,4(3-methoxy)-GlcNAc-O-NM, per-O-acetylated 3-methoxy-GlcNAcβ1,3Gal-O-benzyl (Bn), or per-O-acetylated 4-methoxy-GlcNAcβ1,3Gal-O-Bn. In a further detailed embodiment, the disaccharide is GlcNAcβ3Galβ-O-NM; 4'-deoxy-GlcNAcβ3Gal-O-NM; 4'-fluoro-GlcNAcβ3Gal-O-NM; 4'-thio-GlcNAcβ3Gal-O-NM; 4'-methoxy-GlcNAcβ3Galβ-O-NM; 4'-amino-GlcNAcβ3Gal-O-NM; 3'-deoxy-GlcNAcβ3Galβ-O-NM; 3'-fluoro-GlcNAcβ3Gal-Oβ-NM; 3'-thio-GlcNAcβ3Gal-O-NM; 3'-methoxy-GlcNAcβ3Galβ-O-NM; 3'-amino-GlcNAcβ3Galβ-O-NM; 6'-deoxy-GlcNAcβ3Galβ-O-NM; 6'-fluoro-GlcNAcβ3Gal-Oβ-NM; 6'-thio-GlcNAcβ3Gal-O-NM; 6'-methoxy-GlcNAcβ3Galβ-O-NM; 6'-amino-GlcNAcβ3Galβ-O-NM; GlcNAcβ3Galβ-O—R, wherein R=2-naphthalenemethanol (NM), 8-methoxy-NM, 2-benzyl, phenyl, 2-naphthol, 2-naphthalenethiol, 6-hydroxyquinoline, 5-hydroxyindole, cis/trans-decahydro-2-naphthol, or 2-[oxyethylene]$_n$-2-naphthol; GlcN[$^3$H]Acβ3Galβ-O-NM; or GlcNAcβ3Galβ-O-[$^3$H]NM.

In a further embodiment, a pharmaceutical composition comprises a pharmaceutically acceptable carrier and an effective amount of the acetylated disaccharide of the invention. In a further embodiment, a method of treating disease in a mammalian subject comprises administering a therapeutically effective amount of the composition of the invention. In a detailed embodiment, the composition is administered in a dose of from about 0.1 mg/kg to about 20 mg/kg.

In another embodiment, a method for alleviating cancer in a mammalian subject comprises the step of administering to the mammalian subject a therapeutically effective dose of a composition comprising sugar-X-sugar-Y—R, or a pharmaceutically-acceptable salt or prodrug thereof; wherein: the sugars are glucose, galactose, N-acetylglucosamine, glucosamine, N-acetylgalactosamine, galactosamine, sialic acid, fucose or mannose; X is a bridging atom, O, C, S, or N, and wherein X is a 1-2, 1-3, 1-4, or 1-6 linkage with anomeric configuration, α or β, between the sugars; Y is a bridging atom, O, C, S, or N, with anomeric configuration, α or β; R is an aglycone, benzyl, phenyl, naphthol, naphthalenemethanol, indenol, a heterocyclic derivative of indenol, a heterocyclic derivative of naphthol, a heterocyclic derivative of naphthalenemethanol, an alkyl group of 1-16 carbons, or a polyisoprenoid; and wherein, independently, the sugar is O-alkyl, O-acyl, or O-aryl substituted for a hydroxyl group; the sugar is alkyl-, aryl-, epoxy-, amid-, thiol- or halo-substituted for a hydroxyl group; or the sugar is S-alkyl, N-alkyl, S-acyl, N-acyl, C-acyl, S-aryl, or N-aryl substituted for a hydroxyl group; and wherein the cancer in the mammalian subject is alleviated. In a detailed embodiment, the cancer is adenocarcinoma, lung cancer, breast cancer, colon cancer, gastric cancer, prostate cancer or melanoma. In a further detailed embodiment, the cancer is metastatic cancer. In a further detailed embodiment, the composition is administered in a dose of from about 0.1 mg/kg to about 20 mg/kg.

In another embodiment, a method for the inhibiting tumor metastasis in a mammalian subject comprises administration of a therapeutically effective dose of a composition comprising, sugar-X-sugar-Y—R, wherein the sugars are glucose, galactose, N-acetylglucosamine, glucosamine, N-acetylgalactosamine, galactosamine, sialic acid, fucose or mannose; X is a bridging atom, O, C, S, or N, and wherein X is a 1-2, 1-3, 1-4, or 1-6 linkage with anomeric configuration, α or β, between the sugars; Y is a bridging atom, O, C, S, or N, with anomeric configuration, α or β; R is an aglycone, benzyl, phenyl, naphthol, naphthalenemethanol, indenol, a heterocyclic derivative of indenol, a heterocyclic derivative of naphthol, a heterocyclic derivative of naphthalenemethanol, an alkyl group of 1-16 carbons, or a polyisoprenoid; and wherein, independently, the sugar is O-alkyl, O-acyl, or O-aryl substituted for a hydroxyl group; the sugar is alkyl-, aryl-, epoxy-, amid-, thiol- or halo-substituted for a hydroxyl group; or the sugar is S-alkyl, N-alkyl, S-acyl, N-acyl, C-acyl, S-aryl, or N-aryl substituted for a hydroxyl group.

In a detailed embodiment, the disaccharide is per-O-acetylated Galβ1,4GlcNAc-Y—R, per-O-acetylated Galβ1,3GlcNAc-Y—R, per-O-acetylated Galβ1,3GalNAc-Y—R, per-O-acetylated GlcNAcβ1,3Gal-Y—R, per-O-acetylated GlcNAcβ1,3GalNAc-Y—R, per-O-acetylated GlcNAcβ1,6GalNAc-Y—R, or per-O-acetylated GlcNAcβ1,4GlcNAc-Y—R, R is an aglycone, benzyl, phenyl, naphthol, naphthalenemethanol, indenol, a heterocyclic derivative of indenol, a heterocyclic derivative of naphthol, a heterocyclic derivative of naphthalenemethanol, an alkyl group of 1-16 carbons, or a polyisoprenoid. In a further detailed embodiment, the disaccharide is per-O-acetylated Galβ1,4GlcNAc-O-2-naphthalenemethanol (NM), per-O-acetylated GlcNAcβ1,3Gal-O-

NM, per-O-acetylated GlcNAcβ1,3Gal-O-Bn, per-O-acetylated GlcNAcβ1,3Gal-O-Ph, per-O-acetylated GlcNAcβ1,3Gal-O-2-naphthol, per-O-acetylated Galβ1,3GalNAc-O-NM, per-O-acetylated GlcNAcβ1,3GalNAc-O-NM, per-O-acetylated GlcNAcβ1,6GalNAc-O-NM, per-O-acetylated 3-deoxy-GlcNAcβ1,3Gal-O-NM, per-O-acetylated 4-deoxy-GlcNAcβ1,3Gal-O-NM, per-O-acetylated 3-fluoro-GlcNAcβ1,3Gal-O-NM, per-O-acetylated 4-fluoro-GlcNAcβ1,3Gal-O-NM, per-O-acetylated Galβ1,4(3-methoxy)-GlcNAc-O-NM, per-O-acetylated 3-methoxy-GlcNAcβ1,3Gal-O-benzyl (Bn), or per-O-acetylated 4-methoxy-GlcNAcβ1,3Gal-O-Bn. In a further detailed embodiment, the disaccharide is GlcNAcβ3Galβ-O-NM; 4'-deoxy-GlcNAcβ3Gal-O-NM; 4'-fluoro-GlcNAcβ3Gal-O-NM; 4'-thio-GlcNAcβ3Gal-O-NM; 4'-methoxy-GlcNAcβ3Gal-O-NM; 4'-amino-GlcNAcβ3Gal-O-NM; 3'-deoxy-GlcNAcβ3Galβ-O-NM; 3'-fluoro-GlcNAcβ3Galβ-O-NM; 3'-thio-GlcNAcβ3Gal-O-NM; 3'-methoxy-GlcNAcβ3Galβ-O-NM; 3'-amino-GlcNAcβ3Galβ-O-NM; 6'-deoxy-GlcNAcβ3Galβ-O-NM; 6'-fluoro-GlcNAcβ3Gal-Oβ-NM; 6'-thio-GlcNAcβ3Gal-O-NM; 6'-methoxy-GlcNAcβ3Galβ-O-NM; 6'-amino-GlcNAcβ3Galβ-O-NM; GlcNAcβ3Galβ-O—R, wherein R=2-naphthalenemethanol(NM), 8-methoxy-NM, 2-benzyl, phenyl, 2-naphthol, 2-naphthalenethiol, 6-hydroxyquinoline, 5-hydroxyindole, cis/trans-decahydro-2-naphthol, or 2-[oxyethylene]$_n$-2-naphthol; GlcN[$^3$H]Acβ3Galβ-O-NM; or GlcNAcβ3Galβ-O—[$^3$H]NM.

In another embodiment, a method for regulating biosynthesis of a naturally occurring polysaccharide in a cell, comprises the step of contacting the cell with a pharmacologically effective amount of a composition comprising, sugar-X-sugar-Y—R, wherein the sugars are glucose, galactose, N-acetylglucosamine, glucosamine, N-acetylgalactosamine, galactosamine, sialic acid, fucose or mannose; X is a bridging atom, O, C, S, or N, and wherein X is a 1-2, 1-3, 1-4, or 1-6 linkage with anomeric configuration, α or β, between the sugars; Y is a bridging atom, O, C, S, or N, with anomeric configuration, α or β; R is an aglycone, benzyl, phenyl, naphthol, naphthalenemethanol, indenol, a heterocyclic derivative of indenol, a heterocyclic derivative of naphthol, a heterocyclic derivative of naphthalenemethanol, an alkyl group of 1-16 carbons, or a polyisoprenoid, and wherein, independently, the sugar is O-alkyl, O-acyl, or O-aryl substituted for a hydroxyl group; the sugar is alkyl-, aryl-, epoxy-, amid-, thiol- or halo-substituted for a hydroxyl group; the sugar is O-acyl, S-acyl, N-acyl or C-acyl substituted for a hydroxyl group; or the sugar is O-aryl, S-aryl, or N-aryl substituted for a hydroxyl group.

In another embodiment, a method for identifying a therapeutic cancer treatment, comprises the steps of contacting a tumor cell culture with an effective amount of a disaccharide having the structure sugar-X-sugar-Y—R, or a pharmaceutically-acceptable salt or prodrug thereof; wherein the sugars are glucose, galactose, N-acetylglucosamine, glucosamine, N-acetylgalactosamine, galactosamine, sialic acid, fucose or mannose; X is a bridging atom, O, C, S, or N, and wherein X is a 1-2, 1-3, 1-4, or 1-6 linkage with anomeric configuration, α or β, between the sugars; Y is a bridging atom, O, C, S, or N, with anomeric configuration, α or β; R is an aglycone, including but not limited to benzyl, phenyl, naphthol, naphthalenemethanol, indenol, a heterocyclic derivative of indenol, a heterocyclic derivative of naphthol, a heterocyclic derivative of naphthalenemethanol, an alkyl group of 1-16 carbons, or a polyisoprenoid; and wherein, independently, the sugar is O-alkyl, O-acyl, or O-aryl substituted for a hydroxyl group; the sugar is alkyl-, aryl-, epoxy-, amid-, thiol- or halo-substituted for a hydroxyl group; or the sugar is S-alkyl, N-alkyl, S-acyl, N-acyl, C-acyl, S-aryl, or N-aryl substituted for a hydroxyl group; and further comprises the steps of measuring binding of the tumor cells in culture; and identifying the therapeutic cancer treatment for the mammalian subject by decreased binding of the tumor cell in culture. In a detailed embodiment, the tumor cell is an adenocarcinoma cell.

In a further embodiment, the method comprises measuring binding of the tumor cells to a selectin-coated culture dish. In a further embodiment, the method comprises measuring binding of the tumor cells to thrombin-activated platelets. In a further embodiment, the method comprises measuring binding of the tumor cells to tumor necrosis factor α (TNFα)-activated endothelial cells.

In a further embodiment, the method comprises measuring lung colonization of disaccharide treated tumor cells in an immunodeficient mouse, and identifying the therapeutic treatment for the mammalian subject by decreased tumor metastasis in the immunodeficient mouse.

In another embodiment, a method for alleviating a disease state in a mammal believed to be responsive to treatment with a compound that blocks expression of carbohydrate antigens on a surface of a cell, comprises administering to the mammal a therapeutically effective dose of a compound comprising, sugar-X-sugar-Y—R, or a pharmaceutically-acceptable salt or prodrug thereof; wherein the sugars are glucose, galactose, N-acetylglucosamine, glucosamine, N-acetylgalactosamine, galactosamine, sialic acid, fucose or mannose; X is a bridging atom, O, C, S, or N, and wherein X is a 1-2, 1-3, 1-4, or 1-6 linkage with anomeric configuration, α or β, between the sugars; Y is a bridging atom, O, C, S, or N, with anomeric configuration, α or β; R is an aglycone, benzyl, phenyl, naphthol, naphthalenemethanol, indenol, a heterocyclic derivative of indenol, a heterocyclic derivative of naphthol, a heterocyclic derivative of naphthalenemethanol, an alkyl group of 1-16 carbons, or a polyisoprenoid; and wherein, independently, the sugar is O-alkyl, O-acyl, or O-aryl substituted for a hydroxyl group; the sugar is alkyl-, aryl-, epoxy-, amid-, thiol- or halo-substituted for a hydroxyl group; or the sugar is S-alkyl, N-alkyl, S-acyl, N-acyl, C-acyl, S-aryl, or N-aryl substituted for a hydroxyl group.

In a detailed embodiment, the carbohydrate antigen is a ligand for a cell surface receptor. In a further detailed embodiment, the carbohydrate antigen is a Lewis carbohydrate antigen In a further detailed embodiment, the Lewis carbohydrate antigen is a sialyl (sLe$^X$) carbohydrate or a sialyl (sLe$^a$) carbohydrate. In a detailed embodiment, the carbohydrate antigen is a ligand for a selectin. In a further detailed embodiment, the selectin is an E-selectin, P-selectin, or L-selectin.

In a detailed embodiment, the disease state is neoplastic disease. In a further detailed embodiment, the cancer is adenocarcinoma, lung cancer, breast cancer, colon cancer, gastric cancer, prostate cancer or melanoma. In a further detailed embodiment, the neoplastic disease is metastatic disease. In a further detailed embodiment, the disease state is neoplastic disease, metastatic disease inflammation, wound healing, lysosomal storage diseases, atherosclerosis, and diabetes.

BRIEF DESCRIPTION OF THE DRAWINGS

FIG. 2. AcGnG-NM alters cell-surface sialyl Lewis X in LS180 cells.

FIG. 5. Platelet adhesion to cultured tumor cells is reduced following treatment with AcGnG-NM.

FIG. 10. In vitro characterization of LLC cells after disaccharide treatment.

FIG. 13. Peracetylated GlcNAcβ3Gal-NM inhibits spontaneous tumor metastasis.

FIG. 15. Oligosaccharide priming and inhibition of sLe$^x$ expression.

DETAILED DESCRIPTION

Figure 1:
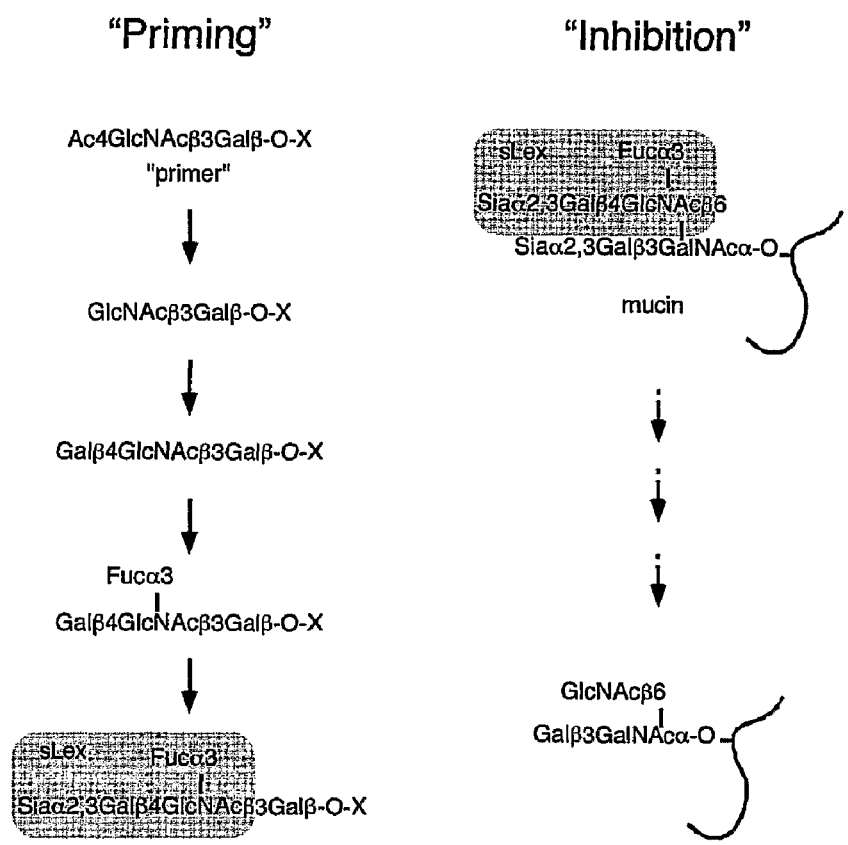
FIG. 1. Inhibiting tumor cell-surface sLe$^X$ using a disaccharide primer.

The invention generally relates to disaccharide compounds and methods for treatment or prevention of disease. The compounds and methods for treatment of the present invention utilize a class of therapeutic agents comprising modified disaccharides, for example, acetylated disaccharides. The mode of action of the acetylated disaccharides is to inhibit glycosyltransferases involved in glycoprotein biosynthesis. The acetylated disaccharides act as inhibitors of the glycosyltransferases involved in production of carbohydrates on a limited set of cells, providing specificity for compounds and methods for treatment or prevention of disease, for example, neoplastic disease or metastatic disease of the present invention, and resulting in minimal side effects. Compounds and methods for treatment or prevention of disease of the present invention include, but are not limited to, neoplastic disease, metastatic disease inflammation, wound healing, lysosomal storage diseases, atherosclerosis, and diabetes.

Compounds and methods for treatment or prevention of disease, e.g., neoplastic disease or metastatic disease, comprise acetylated disaccharides and further include modifications to the sugar that can enhance the inhibitory activity towards specific glycosyltransferases. These modifications include, but are not limited to, deoxygenation, dehydrogenation, epoxidation, alkylation, arylation, amination, or halogenation. Other chemical modifications can be considered in the prevailing art in medicinal chemistry for making analogs of a parent compound, acetylated disaccharide.

Compounds comprising acetylated disaccharides with modifications, as described above, can have improved solubility and pharmacological properties for administration in vivo. In addition, modifications of the acetylated disaccharides are provided wherein the compounds inhibit glycosyltransferase activity (competitive or noncompetitive) without acting as a substrate of the glycosyltransferase. The acetylated disaccharides of the present invention comprise the structure: sugar-X-sugar-Y—R; wherein the sugar is selected from the group consisting of sialic acid, galactose, N-acetylglucosamine, glucosamine, N-acetylgalactosamine, galactosamine, fucose or mannose; X and Y are bridging atoms, which can be oxygen, sulfur nitrogen or carbon; R is an aglycone. In one embodiment the acetylated disaccharide can be peracetylated 4-deoxy GlcNAcβ3Gal-NM (4-deoxy AcGnG-NM). See, for example, U.S. Pat. No. 5,639,734, incorporated herein by reference in its entirety and for all purposes.

Compounds and methods of the present invention comprising disaccharides, e.g., acetylated disaccharides, with modifications are recognized as metabolic intermediates of oligosaccharides, and therefore when fed to cells the acetylated disaccharides are converted into more complex oligosaccharides. The new compounds are modified in specific ways to make them less metabolically active, but they retain sufficient features of the parent compounds such that they still bind to enzymes in the oligosaccharide biosynthetic pathways. Greater specificity can be achieved with these modified analogs. Acetylated disaccharides, and analogs thereof, are intended to inhibit glycosyltransferase reactions that produce certain cell surface glycoconjugates, e.g., glycoproteins and glycolipids. These glycoconjugates facilitate cell adhesion and as such are involved in various biological and physiological processes which can include, but are not limited to, neoplastic disease, metastatic disease inflammation, wound healing, lysosomal storage diseases, atherosclerosis, and diabetes. Thus the acetylated disaccharide compounds through their inhibition of glycoconjugate production can interfere with these types of biological processes and in doing so provide therapeutic treatment of cancer, e.g., neoplastic disease and metastatic disease.

The acetylated disaccharides of the present invention comprise the structure sugar-X-sugar-Y—R, e.g., resembling intermediates in the initiation, elongation and capping reactions of polylactosaminoglycan and sialyl Lewis X (sLe$^x$) assembly. Studies with the compound, peracetylated Galβ1, 4GlcNAc-naphthalenemethanol (AcLacNAc-NM) demonstrated that the acetylated disaccharide compounds serve as primers. As primers they compete for enzyme activity with the normal biosynthetic intermediates inhibiting formation of the normal glycoconjugates. Further studies showed that acetylated disaccharide compounds (acetylated Galβ1, 4GlcNAcβ-O-napthalenemethanol and acetylated GlcNAcβ1,3Gal-O-napthalenemethanol) prime oligosaccharides in a variety of cultured cells of human and murine origin, including various tumor cell lines. In addition, treatment of human tumor cells with these compounds reduces their tumorigenicity, suggesting that the analogs will have similar effects.

Benefits of the present invention include the ability of a class of disaccharides, per-O-acetylated disaccharides and analogs thereof, for example, acetylated forms of GlcNAcβ1, 3Galβ-O-naphthalenemethanol (AcGnG-NM) and peracetylated 4-deoxy GlcNAcβ3Gal-NM (4-deoxy AcGnG-NM), to inhibit adhesion of adenocarcinoma cells to both immobilized recombinant selectins as well as selectins on activated human platelets and endothelia. The results demonstrate that inhibiting tumor cell glycosylation in this way leads to decreased interactions with selectins, increased susceptibility to leukocyte-mediated lysis, and reduction in organ colonization in an experimental model of metastasis.

Clustered presentation of sialyl Lewis X (sLe$^x$) on tumor cell mucins is thought to facilitate metastasis through binding to selectin adhesion receptors expressed on platelets and endothelial cells. Thus, interfering with sLe$^x$ assembly can provide a chemotherapeutic method for treating metastatic disease. Studies have shown that peracetylated disaccharides can act in cells as substrates for the assembly of oligosaccharides related to sLe$^x$ synthesis, and the assembly of oligosaccharides on the disaccharides diverts the assembly of sLe$^x$ from endogenous cell surface glycoconjugates.

The present invention provides compounds and methods for treatment or prevention of neoplastic disease or metastatic disease and demonstrates that treatment of cultured human adenocarcinoma cells with micromolar concentrations of peracetylated disaccharides, for example, (Ac)$_6$GlcNAcβ1,3Galβ-O-naphthalenemethanol (AcGnG-NM, reduces the expression of sLe$^x$ and diminishes binding in vitro to selectin coated dishes, thrombin-activated platelets, and TNF-α activated endothelial cells. Altering glycosylation in this way significantly reduced the ability of tumor cells to distribute to the lungs of wild-type mice over a 3 hour period following intravenous injection. No significant difference in biodistribution was noted following injection of AcGnG-NM-treated tumor cells into P-selectin deficient mice, although the extent of lung seeding was reduced compared to that in wild-type mice. It was demonstrated, in vitro, that normal mouse platelets, but not P-selectin deficient platelets, bound to control tumor cells and protected them from leukocyte-mediated cytolysis. Conversely, treatment of tumor cells with disaccharide markedly reduced the ability of normal platelets to protect them from cytolysis. Finally, in an experimental metastasis model, it was shown that treatment of tumor cells with the disaccharide markedly reduced their lung colonization potential after injection into severe combined immunodeficient mice. The compounds and methods of the present invention represent a class of chemotherapeutic agents for prevention and treatment of metastatic disease.

The present invention provides compositions and methods for treatment utilizing acetylated disaccharides as glycosyltransferase inhibitors for the treatment of disease, e.g., neoplastic disease, metastatic disease inflammation, wound healing, lysosomal storage diseases, atherosclerosis, and diabetes. The compositions and methods of the present invention provide a disaccharide inhibitor of glycosyltransferase comprising the structure: sugar-X-sugar-Y—R, wherein: the sugars are glucose, galactose, N-acetylglucosamine, glucosamine, N-acetylgalactosamine, galactosamine, sialic acid, fucose or mannose; X is a bridging atom, O, C, S, or N, and wherein X is a 1-2, 1-3, 1-4, or 1-6 linkage with anomeric configuration, α or β, between the sugars; Y is a bridging atom, O, C, S, or N, with anomeric configuration, α or β; R is an aglycone, including but not limited to, benzyl, phenyl, naphthol, naphthalenemethanol, indenol, a heterocyclic derivative of indenol, a heterocyclic derivative of naphthol, a heterocyclic derivative of naphthalenemethanol, an alkyl group of 1-16 carbons, or a polyisoprenoid; and wherein, independently, the sugar is O-alkyl, O-acyl, or O-aryl substituted for a hydroxyl group; the sugar is alkyl-, aryl-, epoxy-, amid-, thiol- or halo-substituted for a hydroxyl group; the sugar is O-acyl, S-acyl, N-acyl or C-acyl substituted for a hydroxyl group; or the sugar is O-aryl, S-aryl, or N-aryl substituted for a hydroxyl group. The disaccharide of the present invention further comprises the sugar alkylated with an alkyl group of 1-16 carbon atoms. See for example, U.S. Pat. No. 5,639,734, incorporated herein by reference in its entirety and for all purposes.

Compounds and methods of the invention are useful for treatment of neoplastic disease and metastatic disease, for example, adenocarcinoma. Adenocarcinoma cells have been characterized for the expression of mucin glycoproteins carrying Lewis X structures and are therefore an exemplary primary target of compounds and methods of the invention. Adenocarcinoma of the breast, colon and prostate are some of the most prevalent forms of cancer. Estimated new cancer cases in the United States in the year 2000 are 184,200 for breast, 93,800 for colon and 180,400 for prostate. A significant portion of lung cancers are adenocarcinomas. Melanoma is an exemplary primary target of compounds and methods of the invention since evidence indicates that melanoma is affected by compounds that interfere with selectin binding. The number and types of cancer that the compounds and methods of the invention can be applied to include all neoplastic and metastatic diseases, for example, those diseases characterized by the expression of mucin glycoproteins carrying Lewis-type carbohydrate structures and mediated by binding to selecting. As a treatment for neoplastic disease and metastasis, the compounds of the present invention can be given as adjunct therapy to surgical tumor removal or other forms of cancer chemotherapy. As a treatment for neoplastic disease and metastasis, the compositions of the present invention can be administered in conjunction with other therapeutic compositions that inhibit other biochemical pathways in cancer cells.

The present invention is also directed to a method of treating an inflammatory disease in an individual comprising the step of administering to said individual a therapeutically effective dose of the disaccharide inhibitors of glycosyltransferase, e.g., acetylated disaccharides and analogs thereof in a pharmaceutical composition of the present invention. Generally, the compositions of the present invention can be used to treat a wide variety of inflammatory disease. Representative examples of inflammatory diseases include acute inflammatory diseases and chronic inflammatory diseases. Representative examples of acute inflammatory disease include appendicitis, tonsilitis, delayed hypersensitivity reactions, inflammation due to sepsis, cutaneous inflammation and ischemic reperfusion injury. Representative examples of a chronic inflammatory disease include rheumatoid arthritis. Generally, the composition of the present invention can be administered at any concentration which reduces inflammation in the target individual. Preferably, said composition is administered in a dose of from about 0.1 mg/kg to about 20 mg/kg.

The compounds and methods of the invention can act, for example, by reducing the presence of sialylated carbohydrates on the surface of the cell, such as sialylated Lewis X and sialylated Lewis A. Sialylated carbohydrates form components of ligands that bind to cell adhesion receptors, called selecting. When the ligands are presented on cell surface glycoconjugates, they facilitate adhesion to cells that express cell surface selectin receptors. Most of the naturally occurring selectin ligands are mucin-type glycoproteins that consist of protein cores linked through glycosidic bonds to numerous carbohydrate chains (glycans) that can contain sLex structures.

The carbohydrate antigens include, but are not limited to, ABO, Colton (AQP1), Diego (SLC4A1), Duffy (FY), Hh (FUT1, FUT2), Kell (Kel, XK), Kidd/JK (SLC14A1), Lewis (FUT3, FUT2), Landsteiner-Weiner/LW (ICAM4/LW), Lutheran (LU), MNS (GYPA, GYPB, GYPE), Rh (RHCE, RHD, RHAG), or YT/Cartwright (ACHE). The gene locus for the carbohydrate antigen is in parenthesis. The Lewis carbohydrate antigens include, but are not limited to, H, Le$^a$, sialyl Le$^a$, Le$^b$, Le$^x$, sialyl Le$^x$, Le$^y$ or sialyl Le$^y$. In a detailed embodiment the Lewis carbohydrate antigen is sialyl Le$^x$ (sLe$^x$) or sialyl Le$^y$ (sLe$^y$).

A prominent feature of neoplastic disease is the increased expression of mucins and changes in glycosylation activity in neoplastic cells, including sLex expression that enhance adhesion between tumor cells and selectin-bearing cells such as endothelial cells (E- and P-selectins), platelets (P-selectins) and lymphocytes (L-selectins). Adhesion of tumor cells through interaction with selectin receptors is thought to facilitate cancer progression in a number of ways. First, binding of E- and P-selectins on activated vascular endothelial cells to sLex containing structures on mucin bearing tumor cells can facilitate the transport (extravasation) of tumor cells from the blood to other tissues where the tumor cells can seed secondary tumors (metastasis). Second, similar cell surface binding interactions between tumor cells, leukocytes and platelets can form cell aggregates in the circulation, and these emboli can lodge in the small blood vessels. Third, the association of leukocytes and platelets can provide growth factors that stimulate tumor cell growth or evasion within the immune system. Fourth, evidence suggests that interaction of vascular cells with selectins can be critical for tumor angiogenesis and so this can also be inhibited by the compositions of the invention.

"Metastasis" refers to a multistep cascade involving the migration of tumor cells from their site of origin, evasion of host defense systems, and subsequent seeding of distant organs. During metastatic dissemination, blood-borne tumor cells interact with platelets and leukocytes forming neoplastic emboli that can arrest in the microvasculature and adhere to the endothelium. Tumor cell-host cell adhesion is mediated in part through a family of cell surface carbohydrate binding proteins called selectins. P-selectin on platelets facilitates platelet binding to tumor cells ("cloaking"), which may prevent tumor cell lysis by elements of the innate immune system. P- and E-selectins on the endothelium may help anchor tumor cell-platelet emboli in the microvasculature. L-selectin-mediated adhesion of lymphocytes may result in local secretion of cytokines and growth factors that aid in secondary tumor growth.

"Aglycone" refers to substrates that lack a sugar moiety and that are useful in the present invention.

"Epoxy" refers an oxygen atom bound to two linked carbon atoms Generally, any cyclic ether, but commonly applied to a 3-membered ring; specifically, a three-membered ring is an oxirane, a four-membered ring is an oxetane, a five-membered ring is an oxolane, and a six membered ring is an oxane; oxiranes are commonly produced from peracids acting on alkenes.

"Alkyl" refers to a hydrocarbon radical of the general formula $C_nH_{2n}+1$.

The disaccharides can be acylated with, e.g., acetyl, butyryl or benzoyl groups to reduce their hydrophilicity and make them permeable to cell membranes. Two of the disaccharides, for example, acetylated Galβ1-4GlcNAcβ-O-naphthalenemethanol and acetylated GlcNAc β1-3Galβ-O-naphthalenemethanol, have been shown to prime oligosaccharides in cultured cells and to inhibit the formation of sialyl Lewis X in HL-60 human promyelocytic leukemia cells, LS180 human colon carcinoma, murine Lewis lung carcinoma, B16 murine melanoma. The various disaccharides described above and their acylated or aryl derivatives are logical extensions of the present invention. In addition, analogs of the above compounds in which critical hydroxyl groups are missing or alkylated would bind to glycosyltransfersase and inhibit their activity.

The disaccharide inhibitors of glycosyltransferase, e.g., acetylated disaccharides and analogs thereof, of the present invention can also contain a methyl group attached to a hydroxy group. For example, a methyl group can be attached to any of the hydroxyl groups of the sugars. In addition, the sugar can have a sulfur substituted for an oxygen. For example, it can be preferably to substitute the 5-OH group of the sugar with a sulfur atom.

Representative examples of the disaccharide inhibitors of glycosyltransferase, e.g., acetylated disaccharides, and analogs thereof, of the present invention include, but are not limited to, per-O-acetylated Galβ1,4GlcNAc-Y—R, per-O-acetylated Galβ1,3GlcNAc-Y—R, per-O-acetylated Galβ1,3GalNAc-Y—R, per-O-acetylated GlcNAcβ1,3Gal-Y—R, per-O-acetylated GlcNAcβ1,3 GalNAc-Y—R, per-O-acetylated GlcNAcβ1,6GalNAc-Y—R, or per-O-acetylated GlcNAcβ1,4GlcNAc-Y—R, wherein Y is a bridging atom selected from the group consisting of oxygen, sulfur, nitrogen and carbon; and wherein R is an aglycone, including but not limited to benzyl, phenyl, naphthol, naphthalenemethanol, indenol, a heterocyclic derivative of indenol, a heterocyclic derivative of naphthol, a heterocyclic derivative of naphthalenemethanol, an alkyl group of 1-16 carbons, or a polyisoprenoid.

The present invention is also directed to a method of regulating the synthesis of a naturally occurring saccharide in a cell, comprising the step of contacting said cell with a pharmacologically effective amount of the disaccharide inhibitors of glycosyltransferase, e.g., acetylated disaccharides, and analogs thereof, as a pharmaceutical composition of the present invention. Acetylated disaccharides can be designed, using the teachings of the present invention, to disrupt the synthesis of a wide variety of naturally occurring substances, particularly saccharides. For example, the present invention provides a composition which disrupts the synthesis of a saccharide which binds to a selectin. Representative examples of such disaccharides include, but are not limited to per-O-acetylated Galβ1,4GlcNAc-O-2-naphthalenemethanol (NM), per-O-acetylated GlcNAcβ1,3Gal-O-NM, per-O-acetylated GlcNAcβ1,3Gal-O-Bn, per-O-acetylated GlcNAcβ1,3Gal-O-Ph, per-O-acetylated GlcNAcβ1,3Gal-O-2-naphthol, per-O-acetylated Galβ1,3GalNAc-O-NM, per-O-acetylated GlcNAcβ1,3GalNAc-O-NM, per-O-acetylated GlcNAcβ1,6GalNAc-O-NM, per-O-acetylated 3-deoxy-GlcNAcβ1,3Gal-O-NM, per-O-acetylated 4-deoxy-GlcNAcβ1,3Gal-O-NM, per-O-acetylated 3-fluoro-GlcNAcβ1,3Gal-O-NM, per-O-acetylated 4-fluoro-GlcNAcβ1,3Gal-O-NM, per-O-acetylated Galβ1,4(3-methoxy)-GlcNAc-O-NM, per-O-acetylated 3-methoxy-GlcNAcβ1,3Gal-O-benzyl (Bn), or per-O-acetylated 4-methoxy-GlcNAcβ1,3 Gal-O-Bn. Representative examples of such disaccharides further include, but are not limited to GlcNAcβ3Galβ-O-NM; 4'-deoxy-GlcNAcβ3Gal-O-NM; 4'-fluoro-GlcNAcβ3Gal-O-NM; 4'-thio-GlcNAcβ3Gal-O-NM; 4'-methoxy-GlcNAcβ3Galβ-O-NM; 4'-amino-GlcNAcβ3Gal-O-NM; 3'-deoxy-GlcNAcβ3Galβ-O-NM; 3'-fluoro-GlcNAcβ3Gal-Oβ-NM; 3'-thio-GlcNAcβ3Gal-O-NM; 3'-methoxy-GlcNAcβ3Galβ-O-NM; 3'-amino-GlcNAcβ3Galβ-O-NM; 6'-deoxy-GlcNAcβ3Galβ-O-NM; 6'-fluoro-GlcNAcβ3Gal-Oβ-NM; 6'-thio-GlcNAcβ3Gal-O-NM; 6'-methoxy-GlcNAcβ3Galβ-O-NM; 6'-amino-GlcNAcβ3Galβ-O-NM; GlcNAcβ3Galβ-O—R, wherein R=2-naphthalenemethanol (NM), 8-methoxy-NM, 2-benzyl, phenyl, 2-naphthol, 2-naphthalenethiol, 6-hydroxyquinoline, 5-hydroxyindole, cis/trans-decahydro-2-naphthol, or 2-[oxyethylene]$_n$-2-naphthol; GlcN[$^3$H]Acβ3Galβ-O-NM; or GlcNAcβ3Galβ-O-[$^3$H]NM. Generally, the composition of the present invention can be administered at any concentration which regulates the synthesis of a naturally occurring saccharide in a cell in the target individual. Preferably, said composition is administered in a dose of from about 0.1 mg/kg to about 20 mg/kg.

Treatment Regimes

The invention provides pharmaceutical compositions comprising one or a combination of disaccharide inhibitors of glycosyltransferase, e.g., acetylated disaccharides and analogs thereof, with anti-neoplastic or anti-metastatic activity, formulated together with a pharmaceutically acceptable carrier. Some compositions include a combination of multiple (e.g., two or more) acetylated disaccharides of the invention.

In prophylactic applications, pharmaceutical compositions or medicaments of acetylated disaccharides and analogs thereof are administered to a patient susceptible to, or otherwise at risk of a disease or condition (e.g., a neoplastic or metastatic disease) in an amount sufficient to eliminate or reduce the risk, lessen the severity, or delay the outset of the disease, including biochemical, histologic and/or behavioral symptoms of the disease, its complications and intermediate pathological phenotypes presenting during development of the disease. In therapeutic applications, compositions or medicants are administered to a patient suspected of, or already suffering from such a disease in an amount sufficient to cure, or at least partially arrest, the symptoms of the disease (biochemical, histologic and/or behavioral), including its complications and intermediate pathological phenotypes in development of the disease. An amount adequate to accomplish therapeutic or prophylactic treatment is defined as a therapeutically- or prophylactically-effective dose. In both prophylactic and therapeutic regimes, agents are usually administered in several dosages until a sufficient prophylactic or therapeutic response has been achieved. Typically, the prophylactic or therapeutic response is monitored and repeated dosages are given if the response starts to wane.

Acetylated disaccharides and analogs thereof, useful in the present compositions and methods can be administered to a human patient per se, in the form of a prodrug, pharmaceutically acceptable salt, hydrate, solvate, acid salt hydrate, N-oxide or isomorphic crystalline form thereof, or in the form of a pharmaceutical composition where the compound is mixed with suitable carriers or excipient(s) in a therapeutically effective amount.

Pharmaceutically acceptable carriers are determined in part by the particular composition being administered, as well as by the particular method used to administer the composition. Accordingly, there is a wide variety of suitable formulations of pharmaceutical compositions for administering the acetylated disaccharide compositions (see, e.g. *Remington's Pharmaceutical Sciences*, Mack Publishing Co., Easton, Pa. 18$^{th}$ ed., 1990, incorporated herein by reference). The pharmaceutical compositions generally comprise a acetylated disaccharides or analogs thereof in a form suitable for administration to a patient. The pharmaceutical compositions are generally formulated as sterile, substantially isotonic and in full compliance with all Good Manufacturing Practice (GMP) regulations of the U.S. Food and Drug Administration.

Effective Dosages

Effective doses of the acetylated disaccharides and analogs thereof, for the treatment of conditions and diseases, e.g., neoplastic or metastatic disease, described herein vary depending upon many different factors, including means of administration, target site, physiological state of the patient, whether the patient is human or an animal, other medications administered, and whether treatment is prophylactic or therapeutic. Usually, the patient is a human but nonhuman mammals including transgenic mammals can also be treated. Treatment dosages need to be titrated to optimize safety and efficacy.

For administration with a pharmaceutical composition comprising acetylated disaccharides and analogs thereof, the dosage ranges from about 0.0001 to 100 mg/kg, usually from about 0.01 to 40 mg/kg, and more usually from about 0.1 to about 20 mg/kg, of the host body weight. For example dosages can be 1 mg/kg body weight or 10 mg/kg body weight or within the range of 1-10 mg/kg. In some methods, two or more acetylated disaccharides or analogs thereof with different binding specificities to glycosyltransferases are administered simultaneously, in which case the dosage of each acetylated disaccharide or analog thereof administered falls within the ranges indicated. Acetylated disaccharide compositions are usually administered on multiple occasions. Intervals can be irregular as indicated by measuring blood levels of acetylated disaccharides or analogs thereof in the patient. In some methods, dosage is adjusted to achieve a plasma acetylated disaccharide concentration of 1-100 µg/ml. Alternatively, acetylated disaccharides and analogs thereof can be administered as a sustained release formulation, in which case less frequent administration is required. Dosage and frequency vary depending on the half-life of the acetylated disaccharides in the patient. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime of effective doses of the pharmaceutical composition comprising acetylated disaccharides and analogs thereof.

Routes of Administration

Disaccharide inhibitors of glycosyltransferase, e.g., acetylated disaccharides and analogs thereof with anti-neoplastic or anti-metastatic activity, formulated together with a pharmaceutically acceptable carrier, can be administered by parenteral, topical, intravenous, oral, subcutaneous, intraarterial, intracranial, intraperitoneal, intranasal, intramuscular means, or as inhalants. The most typical routes of administration of an acetylated disaccharides or analogs thereof is subcutaneous or intravenous, although other routes can be equally effective. The next most common route is parenteral. In some methods, agents are injected directly into a particular tissue where tumors have developed. In some methods, acetylated disaccharides or analogs thereof are administered as a sustained release composition or device, such as a Medipad™ device.

Agents of the invention can optionally be administered in combination with other agents that are at least partly effective in treating various diseases. For example, in the case of tumor metastasis to the brain, agents of the invention can also be administered in conjunction with other agents that increase passage of the agents of the invention across the blood-brain barrier (BBB). Another example would include treating patients with a known chemotherapeutic agent along with the agent of the invention (combination therapy).

Formulation

Acetylated disaccharides and analogs thereof with anti-neoplastic or anti-metastatic activity, are often administered as pharmaceutical compositions comprising an active therapeutic agent, and a variety of other pharmaceutically acceptable components. See *Remington's Pharmaceutical Science*, 1990 supra. The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation can also include other carriers, adjuvants, or non-toxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

For parenteral administration, compositions of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. The agents of this invention can be administered in the form of a depot injection or implant preparation which can be formulated in such a manner as to permit a sustained or pulsatile release of the active ingredient.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, *Science* 249: 1527, 1990; and Hanes, *Advanced Drug Delivery Reviews* 28: 97-119, 1997.

Additional formulations suitable for other modes of administration include oral, intranasal, and pulmonary formulations, suppositories, and transdermal applications.

For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Topical application can result in transdermal or intradermal delivery. Topical administration can be facilitated by co-administration of the agent with cholera toxin or detoxified derivatives or subunits thereof or other similar bacterial toxins. Glenn et al., *Nature* 391: 851, 1998. Co-administration can be achieved by using the components as a mixture.

Alternatively, transdermal delivery can be achieved using a skin patch or using transferosomes. Paul et al., *Eur. J. Immunol.* 25: 3521-24, 1995; Cevc et al., *Biochem. Biophys. Acta* 1368: 201-15, 1998.

The pharmaceutical compositions are generally formulated as sterile, substantially isotonic and in full compliance with all Good Manufacturing Practice (GMP) regulations of the U.S. Food and Drug Administration.

Toxicity

A therapeutically effective dose of the acetylated disaccharides or analogs thereof described herein will provide therapeutic benefit without causing substantial toxicity.

Toxicity of the proteins described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the acetylated disaccharides or analogs thereof described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition. (See, e.g., Fingl et al., 1975, In: The Pharmacological Basis of Therapeutics, Ch. 1, Kits Also within the scope of the invention are kits comprising the compositions (e.g., acetylated disaccharides and analogs thereof) of the invention and instructions for use. The kit can further contain a least one additional reagent, or one or more additional acetylated disaccharides of the invention. Kits typically include a label indicating the intended use of the contents of the kit. The term label includes any writing, or recorded material supplied on or with the kit, or which otherwise accompanies the kit.

EXEMPLARY EMBODIMENTS

Example 1

Chemoenzymatic Synthesis of Peracetylated GlcNAcβ3Gal-NM

A synthetic protocol to synthesize gram quantities of GlcNAcβ3Gal-NM for animal studies and for making derivatives with different aglycones was developed (Scheme 1). This was accomplished by using a bacterial β3GlcNAc transferase (LgtA) from *N. meningitidis* overexpressed in *E. coli* (Yan et al., *Carbohydr. Res.*, 328, 3-16, 2000). This enzyme catalyzes GlcNAc transfer from UDP-GlcNAc to Gal yielding the β1,3-linked disaccharide with high stereo- and regio-selectivity without the need to protect the functional groups of the sugars (Scheme 1). Because the synthesis can be done with crude bacterial lysates and inexpensive substrates (UDP sugars; Davos Chemical Corp., Germany), preparative scale synthesis of the disaccharide can be done efficiently and at a reasonably low cost. The final disaccharide was chemically peracetylated, its anomeric carbon was converted to the bromide or trichloroacetimidate, and the compound was coupled to naphthalenemethanol, affording peracetylated GlcNAcβ3Gal-NM in 90% yield after ion-exchange and size exclusion chromatography. $^1$H, $^{13}$C and 2-D NMR, elemental analysis and mass spectrometry was used to confirm the structure of the compound, as we have done in the past for other disaccharides (Sarkar et al., *Carbohydr. Res.* 329, 287-300, 2000; Sarkar et al., *Carbohydr. Res.* 279, 161-171, 1995). The method provides large amounts of disaccharide for coupling to different aglycones, which will further experimentation to determine the influence of the aglycone on inhibition of sLe$^x$ formation.

Example 2

Chemical Synthesis of Peracetylated GlcNAcβ3Gal-NM and Peracetylated 4-deoxy-GlcNAcβ3Gal-NM Scheme 2 depicts the completed chemical synthesis of peracetylated 4-deoxy-GlcNAcβ3Gal-NM and depicts the synthetic route for preparing galactose with the 3-hydroxyl group available for β1,3 glycosylation and a glucosaminyl donor suitably substituted at the 4'-position with hydrogen.

Synthesis of the galactosyl acceptor 4 involved acetylation of 1 with pyridine and acetic anhydride affording the diacetate derivative 2 in 97% yield. The removal of the isopropylidene protecting group under acidic conditions and purification of the product by column chromatography afforded compound 3 in 96% yield. Reaction of 3 with triethylorthoacetate in the presence of p-toluenesulfonic acid furnished an orthoester intermediate, which was subsequently converted under acidic conditions to give 4 in 86% yield. $^1$H and $^{13}$C NMR were in accordance with the proposed structure of 4.

The 4-deoxy donor 11 was prepared from thio-D-glucopyranoside 5 according to literature procedures (Lonn, *Carbohydr. Res.* 139, 105-113, 1985; Zhang et al., *Bioorg. Med. Chem.* 4, 1989-2001, 1996). Treatment of 5 with pyridine and acetic anhydride afforded the 3-O-acetyl intermediate. Subsequent removal of the benzylidene protecting group under acidic conditions and selective protection of the primary hydroxyl group at C6 with an acetyl group afforded 9 in 69% yield. Thiocarbonylimidazolylation (TCDI) at the 4-position of 9 and subsequent radical reduction afforded the 4-deoxy glucosaminyl donor 11 in 81% yield.

Scheme 1 (left): Chemoenzymatic synthesis of peracetylated GlcNAcβ3Gal–NM.
Scheme 2 (right): Synthesis of peracetylated 4-deoxy GlcNAcβ3Gal-NM

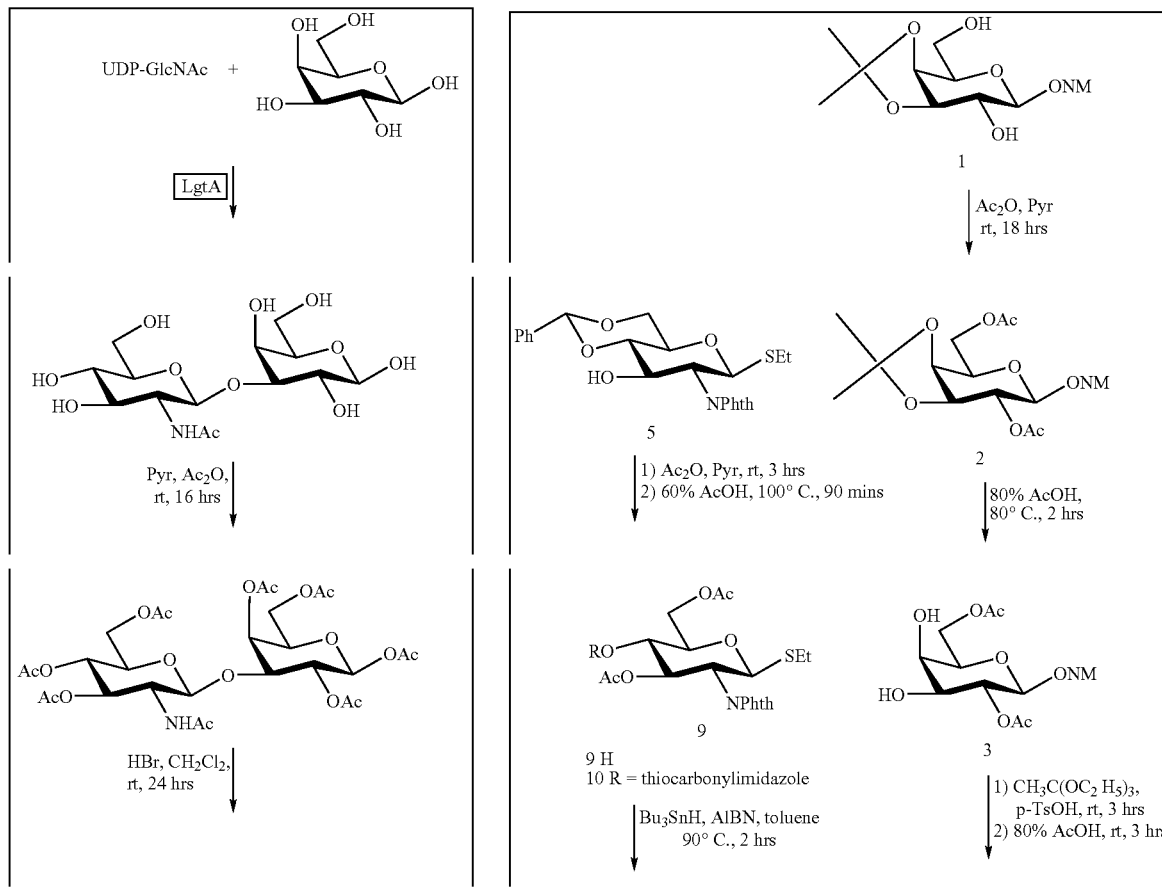

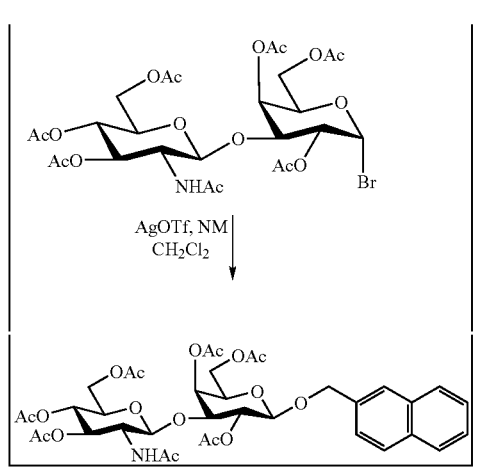

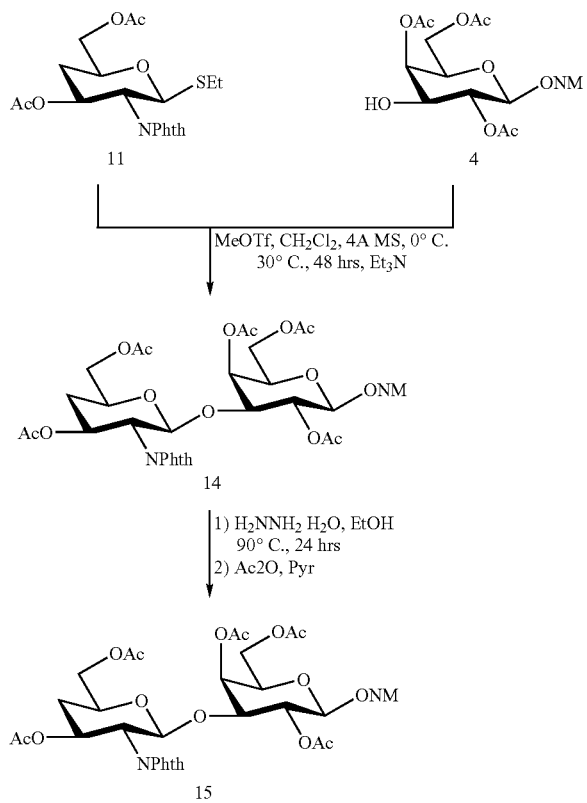

The reaction scheme by Kajihara and co-workers (Kajihara et al., Carbohyd. Res. 306, 361-378, 1998) was adapted to couple 4 with 11 in the presence of methyl triflate to give 14 in 90% yield. Subsequent hydrazinolysis and acetylation in pyridine and acetic anhydride gave 4-deoxy disaccharide 15 in 76% yield. Peaks at δ4.77 (J=7.9 Hz) and δ 4.44 (J=7.9 Hz) in the $^1$H NMR spectra of 15 confirmed the β-glycosidic linkage between the two sugars, and a peak at δ 5.75 (J=6.5 Hz) confirmed the presence of the N-acetyl group of the GlcNAc residue. Approximately 50 mgs was prepared, which is sufficient for the proposed cell culture and enzymology experiments.

Example 3

Synthesis of Disaccharide Analogs of GlcNAcβ3Gal-R

A series of analogs of GlcNAcβ3Gal have been made in which 3'-, 4'- and 6'-OH hydroxyl groups are missing, fluorinated, thiolated, alkylated, or animated. These analogs will potentially inhibit one or more galactosyltransferases involved in sLe$^x$ formation. Analogs will be conjugated to various hydrophobic aglycones and blocked with different ester groups to determine the most effective derivative for inhibiting sLe$^x$ formation. Radioactive disaccharides will be made for radiotracer studies in vivo. Table 1 shows the structure of the peracetylated disaccharides and the analogs that have been or will be synthesized.

TABLE 1

Structure of GlcNAcβ3Gal-R analogs

| Structure (Compound) | Status | Substituents |
|---|---|---|
| GlcNAcβ3Galβ-O-NM | Completed | X = Y = Z = OAc, R = NM |
| 4'-deoxy-GlcNAcβ3Gal-O-NM (15) | Completed | X = H, Y = OAc, Z = OAc, R = NM |
| 4'-fluoro-GlcNAcβ3Gal-O-NM (24) | Underway | X = F, Y = OAc, Z = OAc, R = NM |
| 4'-thio-GlcNAcβ3Gal-O-NM (29) | Planned | X = SH, Y = OAc, Z = OAc, R = NM |
| 4'-methoxy-GlcNAcβ3Galβ-O-NM (32) | Underway | X = OMe, Y = OAc, Z = OAc, R = NM |
| 4'-amino-GlcNAcβ3Gal-O-NM (36) | Planned | X = NH$_2$, Y = OAc, Z = OAc, R = NM |
| 3'-deoxy-GlcNAcβ3Galβ-O-NM (13) | Underway | X = OAc, Y = H, Z = OAc, R = NM |
| 3'-fluoro-GlcNAcβ3Gal-Oβ-NM (18) | Underway | X = OAc, Y = F, Z = OAc, R = NM |
| 3'-thio-GlcNAcβ3Gal-O-NM (41) | Planned | X = OAc, Y = SH, Z = OAc, R = NM |
| 3'-methoxy-GlcNAcβ3Galβ-O-NM (45) | Planned | X = OAc, Y = OMe, Z = OAc, R = NM |

TABLE 1-continued

Structure of GlcNAcβ3Gal-R analogs

| Structure (Compound) | Status | Substituents |
|---|---|---|
| 3'-amino-GlcNAcβ3Galβ-O-NM (47) | Planned | X = OAc, Y = NH$_2$, Z = OAc, R = NM |
| 6'-deoxy-GlcNAcβ3Galβ-O-NM (54) | Planned | X = OAc, Y = H, Z = H, R = NM |
| 6'-fluoro-GlcNAcβ3Gal-Oβ-NM (57) | Planned | X = OAc, Y = F, Z = F, R = NM |
| 6'-thio-GlcNAcβ3Gal-O-NM (61) | Planned | X = OAc, Y = OAc, Z = SH, R = NM |
| 6'-methoxy-GlcNAcβ3Galβ-O-NM (64) | Planned | X = OAc, Y = OMe, Z = OMe, R = NM |
| 6'-amino-GlcNAcβ3Galβ-O-NM (68) | Planned | X = OAc, Y = NH$_2$, Z = NH$_2$, R = NM |
| GlcNAcβ3Galβ-O-R | Underway | X = Y = OAc, R = 2-naphthalene-methanol (NM), 8-methoxy-NM, 2-benzyl, phenyl, 2-naphthol, 2-naphthalenethiol, 6-hydroxyquinoline, 5-hydroxyindole, cis/trans-decahydro-2-naphthol, 2-[oxy-ethylene]$_n$-2-naphthol |
| GlcN[$^3$H]Acβ3Galβ-O-NM | Completed | X = Y = OAc, R = NM |
| GlcNAcβ3Galβ-O-[$^3$H]NM | Planned | X = Y = OAc, R = NM |

The compounds in Table 1 were selected based on information about β4GalTI, also known as lactose synthase. The enzyme adds galactose to GlcNAc-terminated oligosaccharides on glycoproteins and glycolipids, and will produce lactose in the presence of the cofactor, α-lactalbumin (Berger et al., Biochimie., 85, 261-274, 2003). It is part of a multigene family of β4galactosyltransferases (Hennet, Cell Mol Life. Sci., 59, 1081-1095, 2002; Amado et al., Biochim. Biophys. Acta Gen. Subj., 1473, 35-53, 1999). β4GalTI has been studied kinetically, its substrate specificity has been well documented, and X-ray structures with and without UDP-Gal are available (Gastinel et al., EMBO J., 18, 3546-3557, 1999; Ramakrishnan et al., J. Mol. Biol., 310, 205-218, 2001; Ramakrishnan et al., J. Mol. Biol., 318, 491-502, 2002).

β4GalTI will act on free GlcNAc, GlcNAc-terminated oligosaccharides and GlcNAc glycosides, including GlcNAcβ3Gal-R (Table 2). Data presented in the examples below indicate that 4-deoxy-GlcNAcβ3Gal-NM inhibits formation of sLe$^x$ on tumor cells (FIG. 15). Since the acceptor site on the disaccharide was removed, β4galactosylation cannot occur, suggesting that 4-deoxy-GlcNAcβ3Gal-NM may bind to β4GalT1 and prevent its action. Previous studies showed 4-deoxy-Glc can act as a weak inhibitor of β4GalT1 in the presence of lactalbumin (Sinha et al., Carbohydr. Res., 81, 239-247, 1980), but other studies showed that 4-deoxy-GlcNAc-OMe (Hindsgaul, J. Biol. Chem., 266, 17858-17862, 1991) or 4-'deoxy-GlcNAcβ3Gal-OMe did not inhibit the enzyme (Kajihara, Carbohydr. Res., 229, C5-C9, 1992). One possibility for the discrepancy may be that the large aromatic aglycone in our compound may facilitate binding to the enzyme. This explanation is consistent with the observation that active substrates containing aromatic aglycones can inhibit the enzyme from acting on GlcNAc or GlcNAc-OMe with $K_i$ values lower than $K_m$ for GlcNAc (10-22 μM versus 1-10 mM) (Kajihara, Carbohydr. Res., 229, C5-C9, 1992; Chung et al., Bioorg. Med. Chem. Lett., 8, 3359-3364, 1998). Other modifications at 4'-OH of GlcNAcβ3Gal-NM could result in inhibitors as well, including alkylation (Palcic, Carbohydr. Res., 159, 315-324, 1987; Kajihara et al., Carbohyd. Res., 306, 361-378, 1998), halogenation (Kajihara et al., Carbohyd. Res., 306, 361-378, 1998) and amination (Chung et al., Bioorg. Med. Chem. Lett., 8, 3359-3364, 1998; Field et al., Bioorg. Medicinal Chem., 4, 391-394, 1994.)

TABLE 2

Acceptor specificity and inhibitory action of GlcNAc derivatives

| Acceptor | $K_m$ | $V_{max}$ | $K_i$ | Ref |
|---|---|---|---|---|
| Monosaccharides | | | | |
| GlcNAcβ-O-Me | 1.3 mM | NR | — | 1 |
|  | 1.8 mM | 1 (rel) |  | 2 |
|  | 1.5 mM | 1 (rel) |  | 3 |
| 4-deoxy-GlcNAcβ-O-Me | Inactive | Inactive | No inhibition | 1 |
| 4-O-methyl-GlcNAcβ-O-Me | Inactive | Inactive | No inhibition | 4 |
| 4-fluoro-GlcNAcβ-OMe | Inactive | Inactive | No inhibition | 3 |
| 4-thio-GlcNAcβ-OMe | Inactive | Inactive | No inhibition | 3 |
| 4-NH$_2$-GlcNAcβ-OBn | Inactive | Inactive | 0.85 mM | 5 |
| 3-deoxy-GlcNAcβ-O-Me | 4.2 mM | 0.34 (rel) | Not tested | 2, 3 |
| 3-O-methyl-GlcNAcβ-O-Me | 77 mM | 2.4 nmol/min | Not tested | 4 |
| 6-deoxy-GlcNAcβ-O-Me | 0.5 mM | 0.55 (rel) | Not tested | 3 |
| 6-O-methyl-GlcNAcβ-O-Me | 4 mM | 1.1 nmol/min | Not tested | 4 |
|  | 0.5 mM | 0.55 (rel) | Not tested | 2 |
| Acceptor | Km | Vmax | Ki | Ref |
| Disaccharides | | | | |
| GlcNAcβ3Galβ-OMe | 1.1 mM | 1 | — | 2 |
| 4'-deoxy-GlcNAcβ3Galβ-OMe | Inactive |  | No inhibition | 2 |
| 4'-deoxy-GlcNAcβ6Glcβ-OMe | Inactive | — | No inhibition | 3 |
| 3'-F-GlcNAcβ3Galβ-OMe | — | <0.01 (rel) | 2.7 mM | 3 |
| 6'-F-GlcNAcβ3Galβ-OMe | 1.0 | 1 (rel) | Not tested | 2, 3 |
|  | 1 | 0.94 (rel) |  |  |

TABLE 2-continued

Acceptor specificity and inhibitory action of GlcNAc derivatives

| | | | | |
|---|---|---|---|---|
| 6'-thio-GlcNAcβ3Galβ-OMe | Inactive | Inactive | 1 mM | 2 |
| 6'-thio-GlcNAcβ6Glcβ-OMe | 1.2 mM | 0.33 | Not tested | 3 |
| Aglycones | | | | |
| GlcNAcβ-O-1-naphthol | Not reported | Not reported | 22 μM | 6 |
| GlcNAcβ-O-2-naphthol | Not reported | Not reported | 9.5 μM | 6 |
| GlcNAcβ-O-2-bromonaphthol | Not reported | Not reported | 7.6 μM | 6 |
| GlcNAcβ-O-2- methylnaphthol | Not reported | Not reported | 3.5 μM | 6 |
| GlcNAcβ3Galβ-O-2-NM | <10 μM | | Not tested | | rel = data presented as relative to GlcNAcβ-O-Me
*1 Hindsgaul et al., J. Biol. Chem., 266, 17858-17862, 1991.
2 Kajihara, Carbohydr. Res., 229, C5-C9, 1992.
3 Kajihara, Carbohydr. Res., 306, 361-378, 1998.
4 Palcic et al., Carbohydr. Res., 159, 315-324, 1987.
5 Field et al., Bioorg. Medicinal Chem., 4, 391-394, 1994.
6 Chung et al., Bioorg. Med. Chem. Lett., 8, 3359-3364, 1998.

In the following synthetic schemes, each compound will be prepared in 50 mg batches to determine their activity in cell culture and enzyme assays. Active inhibitors will then be prepared in gram quantities for in vivo studies of tumor formation. All of the procedures for preparing the analogs are based on published methods (Kajihara, *Carbohydr. Res.*, 229, C5-C9, 1992; Kajihara, *Carbohydr. Res.*, 247, 179-193, 1993; Lowary, *Carbohydr. Res.*, 251, 33-67, 1994; Zhang et al., *Bioorg. Med. Chem.*, 4, 1989-2001, 1996; Field et al., *Bioorg. Medicinal Chem.*, 4, 391-394, 1994). The overall strategy for making 3'-OH, 4'-OH and 6'-OH derivatives of GlcNAcβ3Gal-NM is to generate key building blocks and adapt similar chemical approaches for each type of modification (deoxygenation, fluorination, thiolation, alkylation, and amination). $^1$H and $^{13}$C-NMR, elemental analysis and mass spectrometry will be used to confirm the structure of all new compounds as was done for other glycosides (Sarkar et al., *J. Biol. Chem.*, 272, 25608-25616, 1997; Sarkar et al., *Carbohydr. Res.*, 329, 287-300, 2000; Sarkar et al., *Carbohydr. Res.*, 279, 161-171, 1995; Lugemwa et al., *J. Biol. Chem.*, 271, 19159-19165, 1996).

The rationale for choosing deoxy-, fluoro-, thio-, methoxy-, and amino-derivatives of GlcNAcβ3Gal-NM is the following: The deoxy derivative should lack activity as an acceptor for β4GalTI since the accepting hydroxyl group is missing. If removal of this hydroxyl does not affect binding, then the derivative could act as a competitive inhibitor. Fluorine is an isostere of oxygen and can form multiple hydrogen bonds with donors, but it cannot act as an glycosyl acceptor. Thus, comparing the deoxy and fluoro derivatives can provide insight into the relative importance of the hydroxyl group in binding. The thio derivatives provide a strong hydrogen bond donor. The methoxy derivatives provide a way to sterically block the active site. For example, a trisaccharide containing a methyl group on an adjacent non-reacting hydroxyl group was found to be a good competitive inhibitor of GlcNAc transferase V ($K_i < K_m$) (Khan, *J. Biol. Chem.*, 268, 2468-2473, 1993). The amino derivatives provide a way to probe for anionic groups in the active site. At neutral pH, the amino group would be protonated, potentially replacing an enzyme-acceptor hydrogen bond with a charge-charge interaction (Chung et al., *Bioorg. Med. Chem. Lett.*, 8, 3359-3364, 1998; Field et al., *Bioorg. Medicinal Chem.*, 4, 391-394, 1994). For example, a disaccharide with similar modification inhibits blood group A glycosyltransferase with a $K_i$ of 200 nM (Lowary, *Carbohydr. Res.*, 251, 33-67, 1994; Laferte et al., *Eur. J. Biochem.*, 267, 4840-4849, 2000).

Synthesis of peracetylated GlcNAcβ3Gal-NM analogs modified at 4'-OH (Scheme 3). The following compounds will be made: 4'-fluoro-, 4'-thio-, 4'-methoxy-, and 4'-amino- GlcNAcβ3Gal-NM. In the example above, the synthesis of peracetylated 4'-deoxy-GlcNAcβ3Gal-NM was discussed (Scheme 1).

The synthetic route for 4-fluoro-GlcNAcβ3Gal-NM 24 is outlined in Scheme 3. The 4-fluoro donor 22 will be prepared from thioethyl-D-glucopyranoside 19 according to literature procedures (Zhang et al., *Bioorg. Med. Chem.*, 4, 1989-2001, 1996). Compound 19 will be treated with acetic anhydride and pyridine to afford 3-O-acetyl derivative 20. The next two steps in the synthesis involve the removal of the benzylidene protecting group (mild acid) and acetylation (pyridine and acetic anhydride) of the 6-OH group to give 21. The free 3-OH group in 21 will then be treated with (diethylamino) sulfur trifluoride (DAST) to give the 4-fluoro donor 22. Coupling of 4 (Scheme 1) with 22 in the presence of methyl triflate will give the disaccharide intermediate 23. Hydrazinolysis and N-acetylation in pyridine should give 4'-fluoro-GlcNAcβ3Gal-NM 24 (Scheme 3).

Scheme. 3. Synthesis of peracetylated 4-hydroxyl glucosaminyl donors

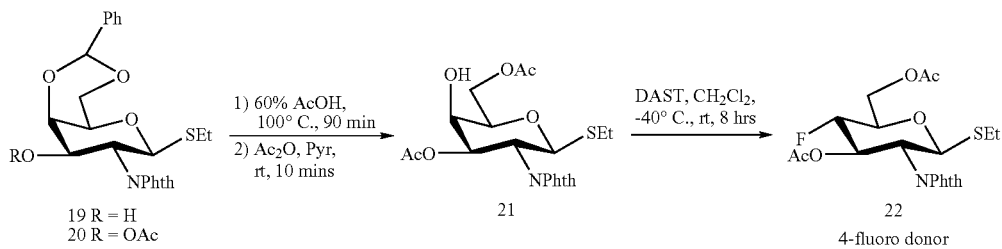

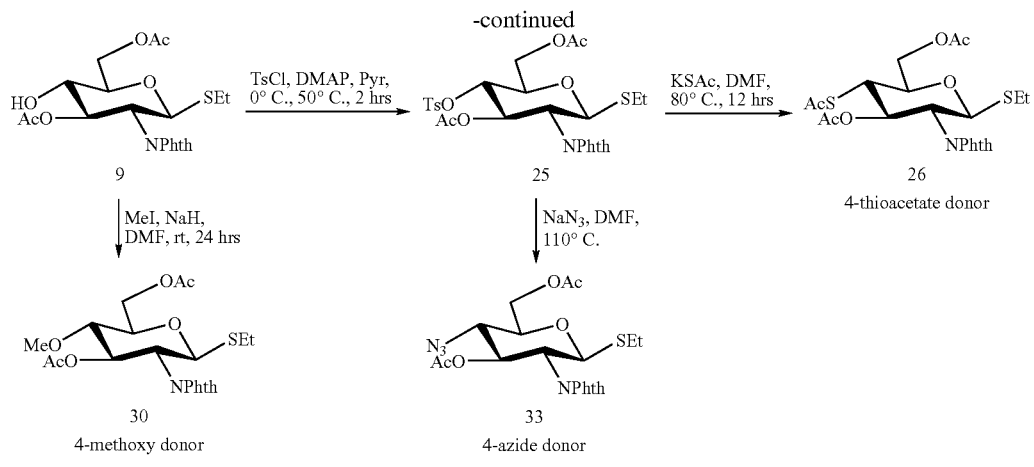

4-thioacetate donor 4-methoxy donor 4-azide donor

To generate the 4-thioacetate donor 26, the 4-alcohol 9 (Scheme 1) will be converted to the 4-tosylate 25 (Scheme 3) using p-toluenesulfonyl chloride in pyridine. The 4-tosylate will be treated with potassium thioacetate to give 26. Coupling of 26 with galactosyl acceptor 4 (Scheme 1) in the presence of methyl triflate followed by hydrazinolysis, N-acetylation and S-deacetylation using $NH_4OH$ in the presence of DL-dithiothreitol should give 4'-thio-GlcNAcβ3Gal-NM 29. To generate the 4-methoxy donor 30, the 4-alcohol 9 will be methylated using methyl iodide and NaH in DMF (Lowary, *Carbohydr. Res.*, 251, 33-67; 1994). (Scheme 3). Coupling of 30 with galactosyl acceptor 4 (Scheme 1) in the presence of methyl triflate followed by hydrazinolysis and N-acetylation should give 4'-methoxy-GlcNAcβ3Gal-NM 32.

The synthesis of the 4'-amino-GlcNAcβ3Gal-NM involves generating the 4-azide donor 33 by reacting the 4-tosylate intermediate 25 with sodium azide. Coupling of 33 with galactosyl acceptor 4 (Scheme 1) in the presence of methyl triflate, followed by hydrazinolysis, N-acetylation and hydrogenation should give the 4'-amino-GlcNAcβ3Gal-NM 36.

Synthesis of peracetylated GlcNAcβ3 Gal-NM modified at 3'-OH (Scheme 4). The following compounds will be made: 3'-deoxy-, 3'-fluoro-, 3'-thio-, 3'-methoxy-, and 3'-amino-GlcNAcβ3Gal-NM. The rationale for preparing these particular derivatives was provided above for scheme 3. Disaccharides containing a bulky constituent at the 3'-hydroxyl position could act as inhibitors of β4GalT1 by sterically precluding the transfer reaction. If β4GalT1 can use these compounds as substrates, then the product might be recognized by one or more α3fucosyltransferases, which require an internal GlcNAc residue for activity. Thus, galactosylated 3'-OH analogs (i.e., Galβ4(3'-X)GlcNAcβ3Gal-NM, where X=H, F, SH, OMe, or $NH_2$) could act as fucosyltransferase inhibitors (Palcic, *Carbohydr. Res.*, 159, 315-324, 1987; Kajihara, *Carbohydr. Res.*, 229, C5-C9, 1992).

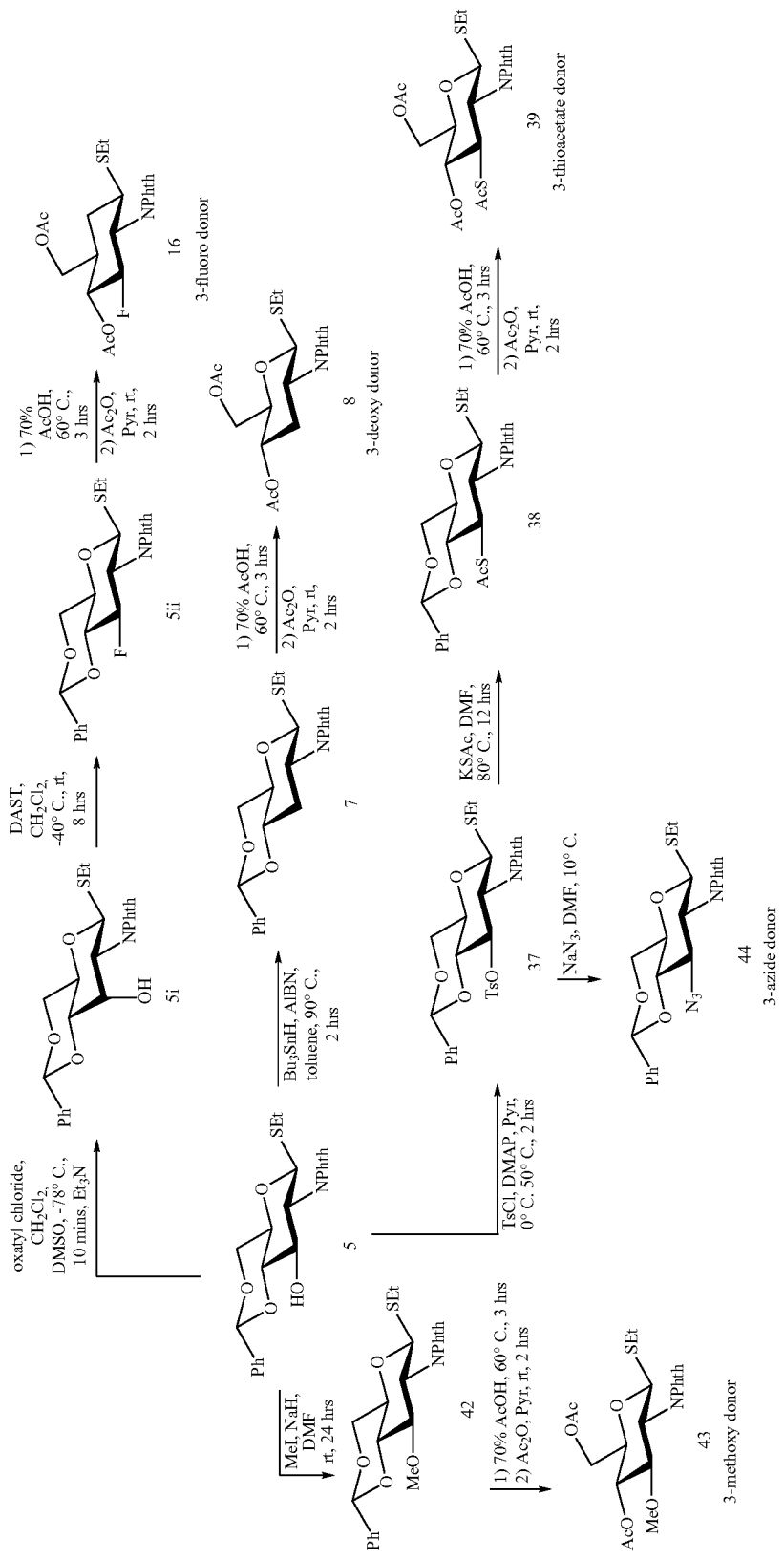
Scheme 4. Synthesis of peracetylated 3-hydroxyl glucosaminyl donors

To prepare the 3-deoxy donor 8, intermediate 5 will be reacted with tributyltin hydride to give intermediate 7. Subsequent removal of the benzylidene protecting group and acetylation of the 6-OH should give 8. The 3-fluoro donor 16 will be synthesized from 5 in three steps (Scheme 4) according to published procedures (Kajihara et al., *Carbohyd. Res.*, 306, 361-378, 1998). 3'-methoxy donor 43 will also be prepared by reacting 5 with methyl iodide and NaH in DMF, followed by removal of the benzylidene and acetylation of the 6-OH to give 43. Coupling of the 3-deoxy donor 8, 3-fluoro donor 16, and 3-methoxy donor 43 with galactosyl acceptor 4 (Scheme 1) in the presence of methyl triflate followed by hydrazinolysis and N-acetylation under reducing conditions should yield the desired 3'-deoxy 13, 3'-fluoro 18, and the 3'-methoxy-45 GlcNAcβ3Gal-NM, respectively.

The 3-thioacetate donor 39 will be made from the tosylate intermediate 37 using potassium thioacetate, followed by removal of the benzylidene and acetylation of 6-OH. Coupling of 39 with galactosyl acceptor 4 (Scheme 1) in the presence of methyl triflate followed by hydrazinolysis, N-acetylation and S-deacetylation using NH₄OH in the presence of DL-dithiothreitol should give 3'-thio-GlcNAcβ3Gal-NM 41.

The synthesis of the 3'-amino-GlcNAcβ3Gal-NM involves generating the 3-azide donor 44 by reacting the 3-tosylate intermediate 37 with sodium azide. Coupling of 44 with galactosyl acceptor 4 (Scheme 1) in the presence of methyl triflate, followed by hydrazinolysis, N-acetylation and hydrogenation should give the 3'-amino-GlcNAcβ3Gal-NM 47.

Synthesis of peracetylated GlcNAcβ3Gal-NM modified at 6'-OH (Scheme 5). The following compounds will be made: 6'-deoxy-, 6'-fluoro, 6'-thio, 6'-methoxy- and 6'-amino-GlcNAcβ3Gal-NM. It is unclear how modifications to the 6' position will affect galactosylation. The available data suggests that the 6'-thio methyl glycoside was a weak inhibitor (Table 2). The other compound (6'-fluoro) was not tested.

The synthetic routes for each of the appropriate glucosaminyl donors are outlined in Scheme 5. The 6-deoxy donor 52 will be prepared from 5 by hydrolysis with 60% acetic acid to give the 4,6-diol 48. Selective 6-O-silylation with tert-buytlchlorodimethylsilane followed by 4-O-acetylation will give 49. O-Desilylation with 60% acetic acid will give the desired 6-alcohol 50, that will be subsequently converted to the 6-tosylate 51 using p-toluenesulfonyl chloride in pyridine. The 6-tosylate will be treated with sodium iodide, followed by homolytic reduction with tributyltin hydride to give the 6-deoxy donor 52. The 6-fluoro donor 55 will be derived from the 6-alcohol 50 by treatment with DAST. The 6-OMe donor 62, will also be derived from the 6-alcohol 50 using methyl iodide and NaH in DMF. Coupling of the 6-deoxy donor 52, 6-fluoro donor 55 and 6-methoxy donor 62 with galactosyl acceptor 4 in the presence of methyl triflate and subsequent hydrazinolysis and acetylation will give the desired 6'-deoxy-54, 6'fluor 57, and 6'-methoxy-64 derivatives of GlcNAcβ3Gal-NM, respectively.

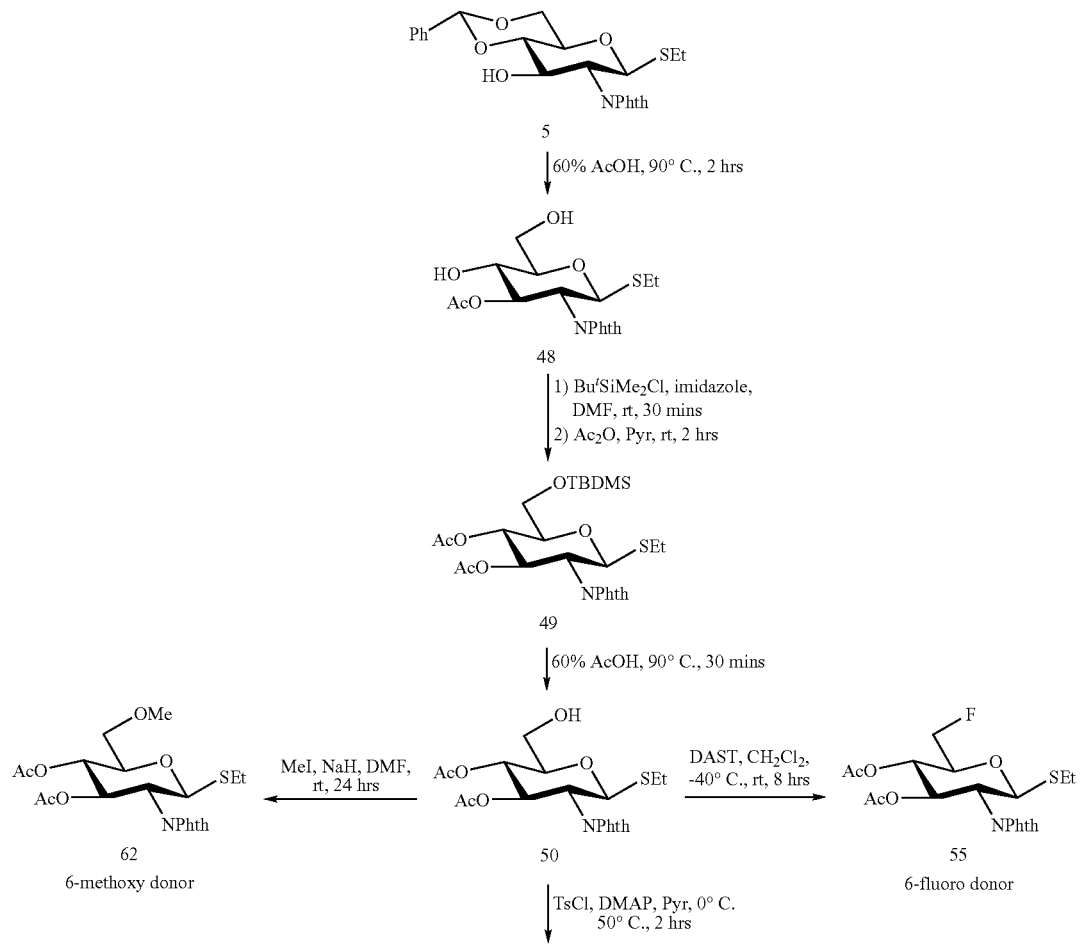

Scheme 5. Synthesis of 6-hydroxyl glucosaminyl donors

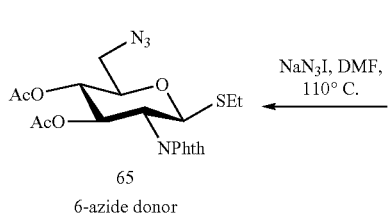

65
6-azide donor

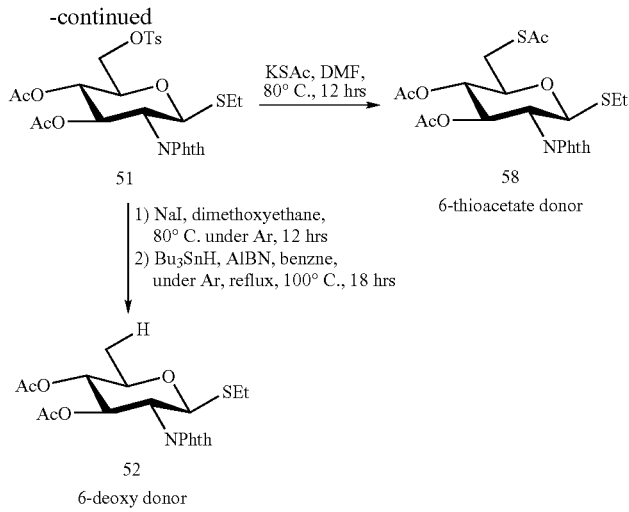

The 6-thioacetate donor 58 will be derived from the 6-tosylate 51 with potassium thioacetate. Coupling of 58 with galactosyl acceptor 4 (Scheme 1) in the presence of methyl triflate followed by hydrazinolysis, N-acetylation and S-deacetylation using NH$_4$OH in the presence of DL-dithiothreitol should give 6'-thio-GlcNAcβ3Gal-NM 61.

The 6-azide donor 65 will be synthesized by treating the 6-tosylate 51 with sodium azide in DMF. Coupling of the azide with galactosyl acceptor 4 followed by hydrazinolysis, acetylation and hydrogenolysis should yield 6'-amino-GlcNAcβ3Gal-NM 68.

Synthesis of radioactive disaccharides. Radiolabeled disaccharides will be synthesized to measure their levels in blood and other tissues. Peracetylated GlcN[$^3$H]Acβ3Gal-NM was synthesized chemically in three steps. GlcNAcβ3Gal-NM was selectively de-N-acetylated using hydrazinolysis (hydrazine, 95° C., 24 h). Re—N-acetylation was accomplished with EDC (1-ethyl-3-(3-dimethylaminopropyl)-carbodiimide) in the presence of [$^3$H]acetic acid (NEN Life Sciences Products). The compound was then acetylated with acetic anhydride in pyridine to give peracetylated GlcN[$^3$H]Acβ3Gal-NM. An alternative synthesis using [$^3$H]acetic anhydride exists, but this reagent is only available by custom order and is quite expensive.

To study what happens to the aglycone, GlcNAcβ3Gal-[$^3$H]NM will be made. The desired compound can be obtained by reduction of commercially available 2-naphthaldehyde (Sigma) with NaB$^3$H$_4$ (NEN Life Science Products) to form $^3$H-naphthalenemethanol [2-$^3$H]NM). Subsequent coupling of GlcNAcβ3Gal-Br (scheme 1) with [2-$^3$H]NM will give GlcNAcβ3Gal-[$^3$H]NM.

Variation of blocking groups. Acetylation of the hydroxyl groups is critical to enhance uptake of the disaccharides, since the large number of hydroxyl groups prevents diffusion through cell membranes. However, other blocking strategies might prove beneficial, e.g., by enhancing the rate of removal of protecting groups. Trichloroacetate esters hydrolyze more rapidly than acetate esters due to the electron withdrawing nature of chlorine (Silverman, The organic chemistry of drug design and drug action, pp. 352-401, Academic Press, San Diego, Calif., 1992). Succinate and acetoxymethyl esters hydrolyze more readily due to the displacement of the acetyl group from the sugar and by intramolecular cyclization (Schultz et al., J. Biol. Chem., 268, 6316-6322, 1993). The choice of blocking group can be critical, since the right balance of aqueous solubility, membrane permeability, and esterolysis must be achieved.

Initially, GlcNAcβ3Gal-NM will be prepared as trichloroacetate, succinate and acetoxymethyl esters. These four compounds will then be tested for their ability to inhibit sLe$^x$ formation in LS180 cells compared to the peracetylated derivatives. If one blocking strategy proves more effective than acetylation, these groups will be introduced into the analog(s).

Synthesis of GlcNAcβ3Gal-R disaccharide with various aglycones. The aglycone plays a key role in priming and inhibition of sLe$^x$ by disaccharides. 1-O-acyl and alkyl glycosides lack activity and long chain forms have undesirable detergent properties. The peracetylated disaccharide GlcNAcβ3Gal-NM contains naphthalenemethanol as the aglycone, which has proven to have many advantages, facilitating uptake into cells, binding of oligosaccharide products to C18 Sep Pak cartridges, and detection of products by UV absorption and fluorescence (Sarkar et al., Proc. Natl. Acad. Sci. USA, 92, 3323-3327, 1995; Sarkar et al. Carbohydr. Res., 329, 287-300, 2000; Brown et al., J. Biol. Chem., 278, 23352-23359, 2003). Nevertheless, the aglycone will be changed to test if naphthalenemethanol is optimal for inhibition of β4GalTI in vitro and sLe$^x$ formation in vivo. β4GalTI greatly prefers substrates with aromatic aglycones providing a guide for selection of derivatives to prepare (Chung et al., Bioorg. Med. Chem. Lett., 8, 3359-3364, 1998). In practice, the selection of compounds also depends on availability of suitable reagents, differences in hydrophobicity (as measured by octanol-water partitioning), and past experience with primers (Ding et al., J. Carbohydr. Chem., 18, 471-475, 1999; Miura et al., Glycoconjugate J., 16, 725-730, 1999; Neville et al., Biochem. J., 307, 791-797, 1995; Fritz et al., J. Biol. Chem., 269, 300-307, 1994; Mong et al., Chembiochem., 4, 835-840, 2003).

To generate the different glycosides, a large quantity of GlcNAcβ3Gal has been prepared chemoenzymatically (Scheme 1). The list of aglycones for coupling reactions is given in Table 1. NMR, elemental analysis and mass spectrometry will be used to confirm the structure of each new compound made. To determine the effect of these aglycones, the glycosides will be tested for inhibition of sLe$^x$ and look for comparable and/or better inhibitory potency compared to the parent compound containing naphthalenemethanol. This information will be a guide in preparing corresponding 3'-, 4'- and 6'-modified disaccharides for further study.

A series of 3'-, 4'- and 6'-OH analogs of GlcNAcβ3Gal-R have been made or will be made in which the hydroxyl groups are missing, fluorinated, alkylated, thiolated or animated. Analogs have been conjugated or will be conjugated to various hydrophobic aglycones and blocked with different ester groups to determine the most effective derivative for inhibiting sLe$^X$ formation. Radioactive disaccharides will be made for radiotracer studies in vivo.

Example 4

Cell Adhesion and Cytolytic Assays

Cell culture. Tumor cell lines derived from human colon (LS180, CCL187) or lung (A549, CCL185; A427, CCLHTB53) adenocarcinomas were purchased from American Type Culture Collection (Rockville, Md.). HAL-8 human lung adenocarcinoma cells were provided by O. Matsuo (Kinki University, Japan). Cells were grown in α-MEM medium (LS180), F12 (A549), F12/DMEM (A427), or RPMI 1640 (HAL-8). All media (GIBCO) were supplemented with 10% (v/v) fetal bovine serum (FBS; HyClone Laboratories), L-glutamine (0.3 g/L), streptomycin sulfate (100 μg/mL), and penicillin (100 Units/mL). Cells were passaged every 4-6 days using ATV trypsin solution (GIBCO). Human microvascular endothelial cells (HMVEC) were grown in EBM-2 media (Clonetics) supplemented with 10% FBS, subcultured using a solution of 0.025% trypsin/0.01% EDTA, and harvested on first or second passage for adhesion assays. All cell lines were maintained at 37° C. in a humidified incubator under an atmosphere of 5% $CO_2$ and 95% air.

Peracetylated forms of GlcNAcβ1,3Galβ-O-naphthalenemethanol (AcGnG-NM) and Galβ1,3Galβ-O-naphthalenemethanol (AcGG-NM) were prepared as described. Sarkar, et al., *Carbohydr. Res.*, 329, 287-300, 2000. The compounds were dissolved in dimethylsulfoxide (DMSO) and added to growth medium to achieve the concentrations indicated in the figures. The supplemented medium was then exchanged for the medium in established cultures of cells in order to avoid lysis caused by adding concentrated DMSO directly to the plates. The final concentration of DMSO was adjusted to ≦0.5% (v/v). After the specified number of days, the cells were harvested with 2 mM EDTA in PBS (20 min) and used for the following experiments.

Cell Sorting. To detect the presence or absence of the relevant carbohydrate determinants, cells were stained with CSLEX-1 (anti-sLe$^X$, 5 μg/mL, Becton-Dickinson) or CA-19-9 (anti-Le$^a$, 14.5 μg/mL, Chemicon) and analyzed by flow cytometry (FACScan Becton-Dickinson, Franklin Lakes, N.J.). Approximately $5 \times 10^5$ cells were incubated for 1 h at 4° C. in 100 μL PBS/1% BSA containing CSLEX-1 or CA-19-9 followed by phycoerythrin (PE)-conjugated rabbit anti-mouse IgG (2 μg/mL). As a negative control, cells were treated with non-specific mouse isotype-matched antibody (0.5 μg/mL, Sigma) for 1 h at 4° C. in 100 μL PBS/1% BSA followed by PE-conjugated rabbit anti-mouse IgG (2 μg/mL).

Cell adhesion to immobilized selectins. 96-well plates were coated overnight at 4° C. with recombinant E-selectin (4 μg/ml) or P-selectin (2 μg/ml) (R & D Systems) and blocked with 1% BSA/PBS. LS180 cells were grown for 5 days with various amounts of acetylated disaccharide, harvested, labeled with Calcein AM (5 μM, Molecular Probes) in DMEM/1% FBS, and allowed to settle at room temperature on selectin-coated wells ($5 \times 10^4$ cells/well). Plates were then stirred at 75 rpm for 30 min (Orbit shaker, Lab-Line Instruments) followed by immersion upside-down in a vessel filled with Hank's buffered saline solution (HBSS, Sigma), which allowed non-adherent cells to fall under gravity. St John et al., *J. Immunol Methods*, 170: 159-166, 1994. The wells were then washed by aspiration using HBSS. LS180 cells were less adherent to P-selectin, so the immersion step was not necessary prior to washing. Controls included treating tumor cells for 1 hr at 37° C. with *Arthrobacter ureafaciens* sialidase (AUS, Calbiochem; 20 mU/$1 \times 10^6$ cells) in 0.05 M N-(2-hydroxyethyl)piperazine-N'-(2-ethanesulfonic acid) (HEPES) buffer (pH 6.9), pre-treating selectin-coated wells with anti-E- or P-selectin monoclonal antibody (1 μg/well; Pharmingen), or growing tumor cells in 50 μM of the inactive disaccharide primer, peracetylated Galβ1,3Galβ-O-NM. Fluorescence was measured using a 96-well fluorimeter (CytoFluor II), and the average of triplicate measurements was determined±standard error. Cell viability was judged to be >90% by Trypan blue exclusion at the end of each experiment.

Adhesion of tumor cells to activated human endothelial cells. HMVEC were added to 96-well plates ($1 \times 10^4$ cells/well) in EBM-2 media (Clonetics), and allowed to grow to confluence over 2 days. The cells were activated with TNF-α (20 ng/ml; R&D Systems) for 4 hr at 37° C. Calcein labeled tumor cells, harvested after growth for 5 days in various levels of AcGnG-NM, were added to HMVEC at $2.5 \times 10^4$ cells/well in 100 μl DMEM and allowed to settle for 20 min. The wells were washed twice with cold PBS, and the extent of binding was determined by fluorimetry. In some experiments anti-E-selectin mAb (2 μg/well) was added prior to addition of tumor cells, cells were treated with sialidase (20 mU/$10^6$ cells), or TNF-α was omitted.

Adhesion of activated human platelets to tumor cells. Tumor cells were seeded into 6-well plates ($5 \times 10^4$/well), and allowed to grow into colonies in the presence or absence of 50 μM AcGnG-NM. After 3 days, platelets were isolated from 15 ml of normal human blood collected into 20% (v/v) Acid-Citrate-Dextrose (ACD) anticoagulant. A platelet-rich plasma was prepared by centrifugation and repeated washing using PSG buffer (5 mM HEPES, pH 6.8, 145 mM NaCl, 4 mM KCl, 0.5 mM sodium phosphate, 5.5 mM glucose, 0.5% BSA, and 25 nM prostaglandin E1 [Sigma]). The platelets were then labeled with Calcein AM (5 μM), and counted with a hemocytometer. Wells containing tumor cells were washed with HBSS, and $3 \times 10^6$ platelets were added in 1 ml of HBSS followed by activation with human thrombin (0.8 IU/well; Sigma). The plates were rocked for 10 min, and the wells were washed twice with HBSS, fixed with 5% formalin in HBSS, and analyzed by fluorescence microscopy. Controls included pretreatment of tumor cells with AUS sialidase (20 mU/well in 0.05 N HEPES, pH 6.9, 1 mM $CaCl_2$, 1 mM $MgCl_2$), pretreatment of tumor cells with O-sialoglycoproteinase (2.4 μg/ml; Cedarlane) prior to addition of platelets, addition of anti-P-selectin mAb (10 μg/ml in HBSS) to the platelet suspension prior to thrombin activation and addition to tumor cells, or omission of thrombin.

Platelets bound to tumor cells were visualized by fluorescence microscopy (Nikon Diaphot) equipped with a digital camera (Nikon) linked to an Apple Macintosh computer with Adobe Photoshop software. The fluorescence image showing the platelets was superimposed on a phase-contrast picture of the cells and the number of attached platelets was quantified. A "Platelet Association Index" was generated for each well by dividing the number of tumor-associated platelets by the percent area occupied by tumor cells.

Biodistribution studies in mice. LS180 cells were grown for 3 days in the presence or absence of 50 µM AcGnG-NM. [$^3$H-methyl]thymidine (10 µCi/ml, NEN Life Sciences Products) was added to the medium, and cells were incubated for another 3 days. The cells were then harvested with EDTA, resuspended in sterile 0.9% saline, and injected (1×10$^5$ cells/ 100 µL) into the lateral tail vein of anesthetized (inhaled methoxyflurane, Janssen Pharmaceuticals) 6-8 week-old wildtype C57BL/6 mice or P-selectin deficient mice bred on the same background (Jackson Laboratory). Mayadas et al., Cell, 74: 541-554, 1993. Upon awakening, mice were observed for 3 hours, anesthetized, bled (~200 µL each), sacrificed via cervical dislocation, and dissected for collection of lungs, liver, kidney/adrenals, spleen and brain. The organs were digested at 55° C. overnight with Proteinase K (0.15 µg/ml, Boehringer Mannheim) in 2 mL PBS containing 1% sodium dodecyl sulfate, and homogenized by repeated passage through an 18 gauge needle. The amount of radioactive DNA in the blood and the organ extracts was then determined using an Easy DNA Kit (Invitrogen) and liquid scintillation spectrometry. The total counts in blood were estimated by assuming a total blood volume of 2 mL per mouse. Proper attention has been given to experimental ethical considerations towards animals as prescribed by the Animal Subjects Program at the University of California.

Tumor formation. LS180 cells were grown in the presence or absence of 50 µM AcGnG-NM for 6 days, harvested with EDTA, and resuspended in sterile PBS. Approximately 3×10$^5$ tumor cells in 150 µl PBS were injected into the lateral tail vein of anesthetized 7 week-old immunodeficient mice (Fox Chase SCID; Charles River). The mice were then maintained in microbe-free housing with free access to standard laboratory chow and water, and inspected regularly for any signs of distress. After 4 weeks, mice were euthanized by CO$_2$ asphyxiation under anesthesia, and lungs, livers, brains, kidneys/adrenals, and spleens were fixed in Bouin's solution (Sigma) for 6 hr followed by transfer to 70% ethanol. Lungs for each animal were inspected under a dissecting microscope for the total number of surface tumors. Histologic sections (hematoxylin/eosin) were examined for tumor foci, and representative photomicrographs were taken. The other organs were also reviewed histologically for any tumor foci.

Cytolytic Assays. LS180 cells were grown to near-confluence in the presence or absence of 50 µM AcGnG-NM for 6 days, harvested using 2 mM EDTA/PBS, washed, and resuspended in RPMI 1640 medium containing 10% FBS and 15 µCi Na$_2$$^{51}$CrO$_4$ (435 mCi/mg, Dupont NEN). After 2 hr at 37° C. the cells were then washed twice with medium and placed into a conical 96-well plate (1500 cells/well). Effector cells were prepared from normal C57BL/6 mouse spleens by mincing the tissue and sieving the cells over a fine screen. Red cells were lysed by resuspension in 0.83% NH$_4$Cl in PBS, and the enriched leukocytes were resuspended in RPMI medium containing 10% FBS and 200 U/ml of recombinant human Il-2 (GIBCO). After 3 days of culture, the leukocytes were added to the wells containing tumor cells. Some wells also received platelets (10$^4$ platelets per tumor cell) isolated from pooled whole blood (2-4 mice per group) prepared by the same procedures described above for the isolation of human platelets. Nieswandt, et al., Cancer Res., 59: 1295-1300, 1999. After 3 hr at 37° C., the amount of $^{51}$Cr released was measured by centrifuging the plate at 1500 rpm and taking an aliquot of the supernatant. Spontaneous release ($R_{spont}$) of radioactivity was measured by incubating target cells in RPMI medium only. Maximum release ($R_{max}$) was measured after complete lysis of targets in 2% sodium dodecyl sulfate. Specific lysis was determined according to the equation: Specific Lysis=$(R_{exp}-R_{spon})\times 100/(R_{max}-R_{spon})$, where $R_{exp}$=counts released in the presence of effector cells. In some experiments labeled tumor cells were added to whole human blood (1.6 ml per sample, collected into 20% v/v ACD anticoagulant) and incubated with stirring at 37° C. for 3 hr.

Example 5

Acetylated Disaccharides Inhibit Cell Adhesion In Vitro

Previous studies showed that cells take up and rapidly deacetylate peracetylated disaccharides and assemble oligosaccharides onto the exogenous disaccharide. Sarkar et al., Proc. Natl. Acad. Sci. USA, 92: 3323-3327, 1995; Sarkar et al., J. Biol. Chem., 272: 25608-25616, 1997. The result is reduced cell-surface levels of the relevant endogenous terminal oligosaccharide (e.g., sLe$^X$). FIG. 1 shows inhibition of tumor cell-surface sLe$^X$ using a disaccharide primer. On the left, AcGnG-NM passively enters cells by diffusion, undergoes rapid deacetylation, and acts as a substrate for the assembly of oligosaccharides related to Lewis type antigens. "Priming" in this way inhibits terminal glycosylation on endogenous glycoprotein substrates as shown on the right, resulting in a reduction in cell-surface sLe$^X$. Several disaccharides related to mucin-like oligosaccharides that carry sLe$^X$ determinants were shown to be effective as primers, with peracetylated GlcNAcβ1,3Galβ-O-NM (AcGnG-NM) exhibiting the highest potency. Sarkar et al., Carbohydr. Res., 329: 287-300, 2000. Priming of oligosaccharides in this way inhibited the expression of sLe$^X$ by HL-60 and U-937 cell lines. The effect of the disaccharide on selectin binding and tumor forming properties of LS180 human colon adenocarcinoma cells was examined. These cells were chosen since they express carbohydrate ligands known to bind to E- and P-selectins, and they form lung tumors in an experimental murine model of hematogenous metastasis. Kim et al., Proc. Natl. Acad. Sci. USA, 95: 9325-9330, 1998; Borsig et al., Proc. Natl. Acad. Sci. USA, 98: 3352-3357, 2001; Kim et al., Am. J. Pathol., 155: 461-472, 1999; Mannori et al., Cancer Res., 55: 4425-4431, 1995; Cecconi et al., J. Biol. Chem., 269: 15060-15066, 1994.

Treatment of LS180 cells with AcGnG-NM reduces cell-surface sLe$^X$, but not sLe$^a$. Tumors of the gastrointestinal tract generally express relatively high levels of both sLe$^X$ as well as sLe$^a$. Since either of these oligosaccharides may mediate binding to selectins, experiments examined whether treatment of LS180 cells with AcGnG-NM could inhibit expression of either oligosaccharide on the cell surface. Treatment with 50 µM AcGnG-NM resulted in significant inhibition of cell-surface sLe$^X$, whereas it had no effect on cell-surface sLe$^a$. As shown in FIG. 2, AcGnG-NM alters cell-surface sialyl Lewis X in LS180 cells. LS180 cells were grown in the presence of 50 µM AcGnG-NM, harvested with EDTA, stained with monoclonal antibodies (CSLEX-1, anti-sLe$^X$ and CA19-9, anti-sLe$^a$) as indicated and analyzed by flow cytometry (Materials and Methods). The average fluorescence value for each sample was normalized to the value obtained from a sample of cells that had not been treated with inhibitor. The value obtained for nonspecific isotype-matched antibody in each case was <10% of the value obtained with CSLEX-1 or CA19-9.

Figure 3:
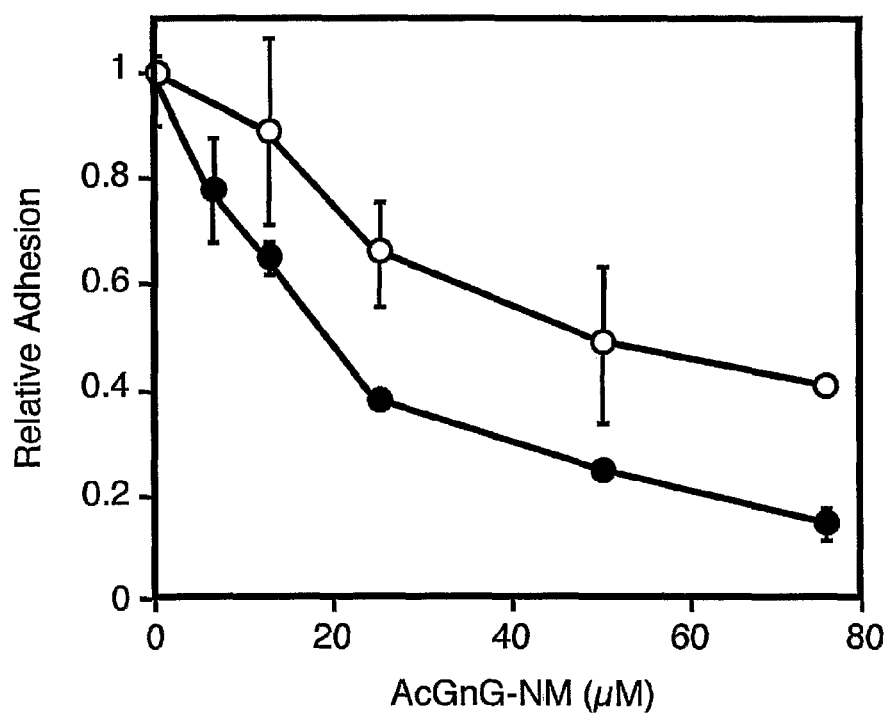
FIG. 3. Altered adhesion of AcGnG-NM treated tumor cells to immobilized selectins.

Adhesion to selectins is altered in disaccharide-treated tumor cells. Treatment of LS180 cells with AcGnG-NM was not toxic to the cells up to 100 µM based on growth curves and exclusion of Trypan blue. However, treatment with the disaccharide inhibited expression of sLe$^X$ on the cell surface in a dose-dependent manner, as measured by ELISA using CSLEX-1 mAb to probe the cell surface. FIG. 3 shows altered adhesion of AcGnG-NM treated tumor cells to immobilized selectins. LS180 colon carcinoma cells were "panned" onto wells precoated with recombinant E- or P-selectin as indicated. Open circles, adhesion to E-selectin; filled circles, adhesion to P-selectin. The extent of adhesion was normalized to the value obtained for cells not treated with disaccharide. Samples treated with sialidase, anti-E- or anti-P selectin mAb, or 50 µM of the inactive disaccharide primer acetylated-Galβ1,3Galβ-O-NM gave values of 0.28-0.32, 0.05-0.33, 0.95-1.1, respectively. Each experimental condition was done in quadruplicate and the average values±standard errors are given. When the disaccharide was removed from the culture medium, the ligand reappeared on the cell surface with a $t_{1/2}$ of approximately 6 hr, indicating that no permanent damage to the cells had occurred. Inhibiting the expression of $sLe^x$ in this way reduced the ability of LS180 cells to adhere to recombinant E- and P-selectin immobilized on plastic dishes. Adhesion to P-selectin was more sensitive to the inhibitor than adhesion to E-selectin under these conditions. The inhibitory effect of AcGnG-NM was specific since incubation of cells with acetylated Galβ1,3Galβ-O-NM (AcGG-NM) had no effect on expression of $sLe^x$ or adhesion to either selectin conjugate See FIG. 3. The maximum extent of inhibition approached the values obtained when the cells were pre-treated with sialidase or blocking antibody to the corresponding selectin.

Figure 4:
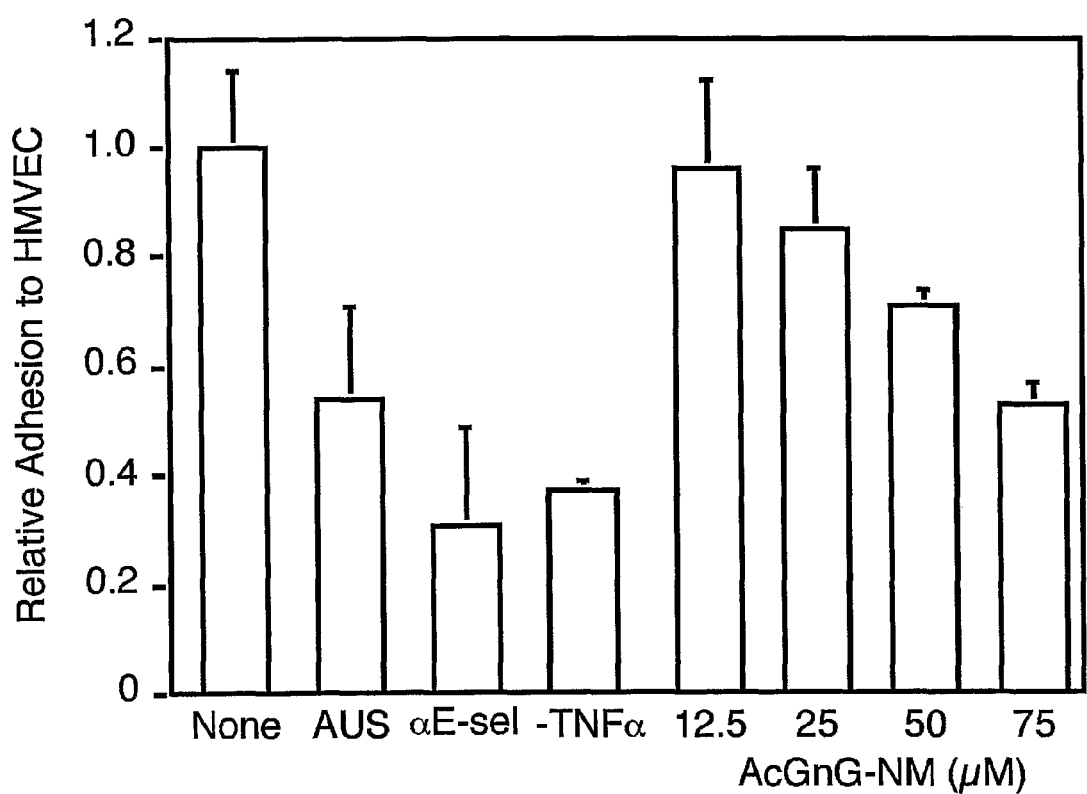
FIG. 4. Altered adhesion of AcGnG-NM treated tumor cells to cultured human microvascular endothelial cells (HM-VEC).

AcGnG-NM inhibits adhesion to activated endothelia and platelets. In the circulation, tumor cells can encounter E- and P-selectins expressed on endothelial cells, P-selectin on platelets, and L-selectin on leukocytes. Since the presentation of receptors on cells may differ from their arrangement when immobilized on plastic surfaces, LS180 cells were challenged to bind to E-selectin expressed on TNF-α activated human microvascular endothelial cells (HMVEC). FIG. 4 shows altered adhesion of AcGnG-NM treated tumor cells to cultured human microvascular endothelial cells (HMVEC). HMVEC were activated with TNF-α and overlaid with Calcein-loaded LS180 cells. The extent of adhesion was normalized to the value obtained for cells not treated with disaccharide. Some samples were treated with sialidase (AUS) or anti-E selectin antibody, or the HMVEC were not activated with TNF-α. Each condition was done in triplicate and the values were averaged. In this system, adhesion was mostly dependent on E-selectin expression since blocking antibody or absence of TNF-α stimulation dramatically lowered the extent of adhesion. AcGnG-NM inhibited adhesion with a dose-response similar to that observed using immobilized receptor. See FIG. 3. The maximum extent of inhibition was similar to that obtained after treatment of the tumor cells with sialidase, which destroys $sLe^x$, or by using a blocking antibody to E-selectin.

Experiments examined how the acetylated disaccharide compounds affected adhesion of platelets, as mediated by P-selectin. FIG. 5 shows platelet adhesion to cultured tumor cells is reduced following treatment with AcGnG-NM. LS180 cells were grown on 6-well plates as multi-cell "islands" in the presence or absence of 50 µM AcGnG-NM for 3 days. Human platelets were labeled with Calcein, activated with human thrombin and allowed to adhere to the tumor cells. The number of adherent platelets/area occupied by tumor cells was determined (Platelet Adhesion Index, PAI) PAI values for all wells were normalized to that for platelet adhesion to untreated tumor cells. Some samples of tumor cells were treated with sialidase (AUS), O-sialoglycoproteinase (OSGPase), anti-P selectin antibody, or with platelets that had not been activated with thrombin. See FIG. 5A, LS180 colon carcinoma cells; FIG. 5B, A549 lung adenocarcinoma cells; FIG. 5C, A427 lung adenocarcinoma cells. Platelets were loaded with fluorescent Calcein dye and the number of platelets adhering to islands of cultured LS180 cells was quantified by fluorescence microscopy. AcGnG-NM caused a dose-dependent inhibition of platelet adhesion, with 60% reduction achieved after treatment of the tumor cells with 50 µM of disaccharide. See FIG. 5A. The extent of inhibition was comparable to that achieved by treating tumor cells with sialidase and O-sialoglycoproteinase, which requires clustered oligosaccharide chains for cleavage of the underlying protein core. Mannori et al., *Cancer Res.*, 55: 4425-4431, 1995; Mellors et al., *Methods Enzymol.*, 248: 728-740, 1995. The extent of inhibition was not as great as that achieved by blocking antibody or by omitting thrombin activation, suggesting that the disaccharide did not fully suppress expression of $sLe^x$ or alternatively that non-sialic acid containing ligands for P-selectin exist. Similar effects were observed in studies of two lung adenocarcinoma cell lines, A549 and A427. See FIGS. 5B and 5C, respectively. These cells also express selectin ligands and $sLe^x$ determinants, but they varied in their response to sialidase and AcGnG-NM treatment.

Figure 6A:
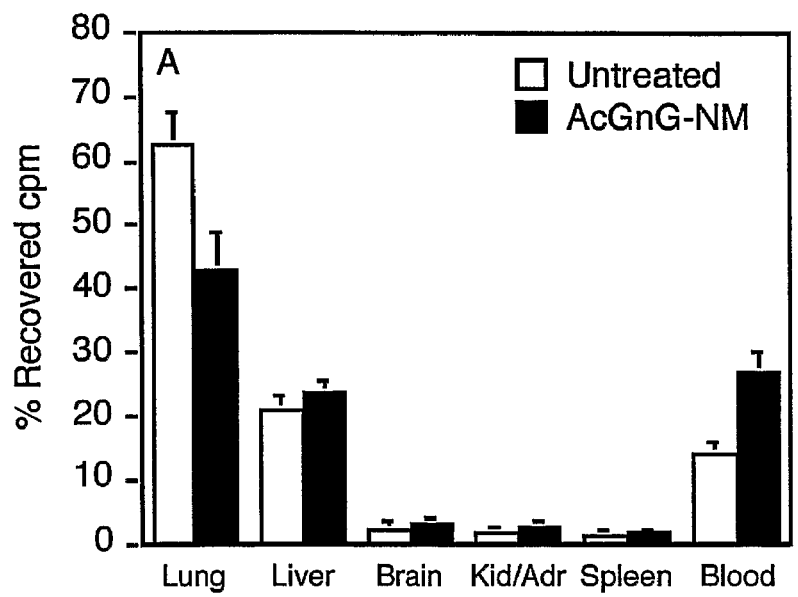
FIG. 6. Altered biodistribution of inhibitor-treated tumor cells in mice.
Figure 6B:
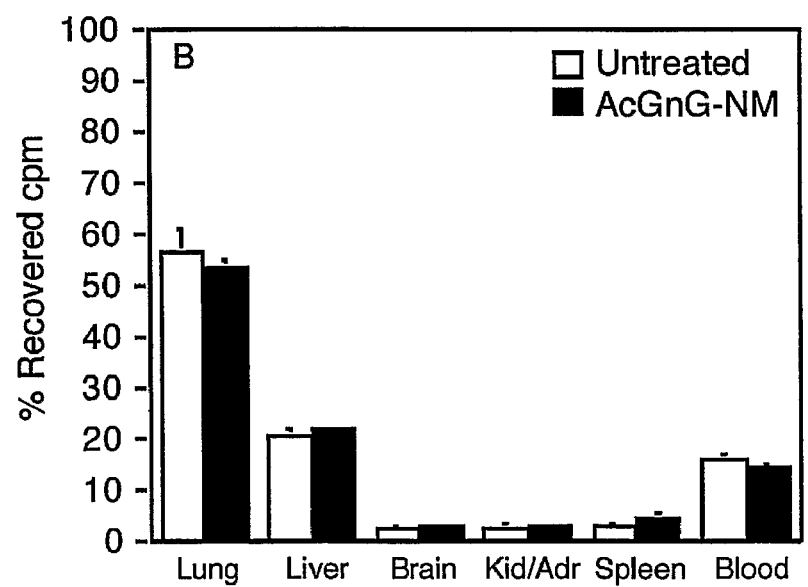

Altered biodistribution of AcGnG-NM treated tumor cells. The lung is the major "first-pass" adhesion target for tumor cells introduced into the venous circulation. FIG. 6 shows altered biodistribution of inhibitor-treated tumor cells in mice. Radiolabeled cells were injected into the lateral tail vein of C57BL/6 mice, and allowed to circulate for 3 hours. Mice were sacrificed and DNA was extracted from organ homogenates and whole blood. The counts were normalized to the total recovered counts, which typically represented 80-90% of the injected samples. In FIG. 6A, each value represents the average recoveries from 4 wildtype mice±standard deviation from the mean. In FIG. 6B, the experiment was repeated in P-selectin deficient C57BL/6 mice that were injected with either control- or AcGnG-NM-treated LS180 cells. Ten minutes after injection of radiolabeled LS180 cells into the lateral tail-vein of mice, over 90% of the recovered counts were found in the lung. After 3 hrs, about 60% of recovered counts remained in the lung, ~20% in the liver, ~15% in the blood, and lesser amounts in other organs. See FIG. 6A. Inhibitor-treated cells exhibited a different biodistribution following injection. Seeding of the lungs was substantially reduced and accompanied by a corresponding increase in counts recovered in the blood compartment, without significant differences in seeding of other tissues. When treated and untreated cells were injected into P-selectin deficient mice, no difference was observed in the distribution of the cells although the extent of seeding was reduced compared to wildtype mice. See FIG. 6B. Thus altering either P-selectin or its carbohydrate ligand had similar effects, suggesting that the interaction of the tumor cell glycans with host cellular elements expressing P-selectin affected the fate of the cells.

Figure 7A:
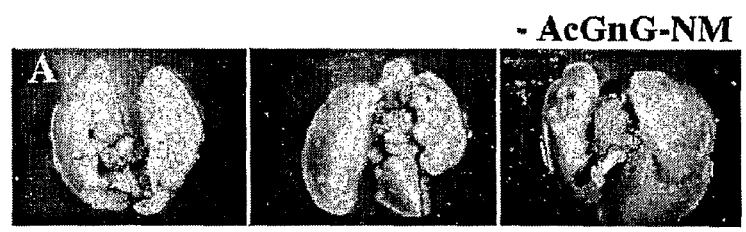
FIG. 7. Metastatic lung tumor formation is inhibited by treatment with AcGnG-NM.
Figure 7B:
Figure 7C:
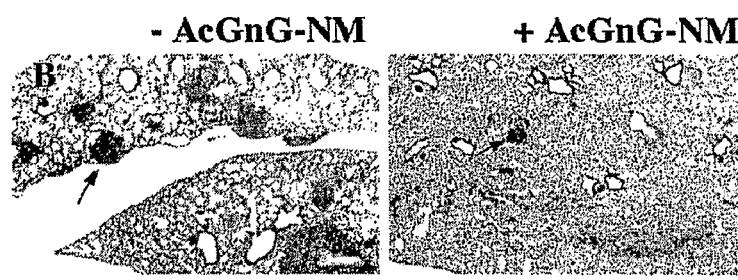

Impairment of metastatic tumor formation. Prior studies have shown that deletion of P-selectin in mice alters the tumorigenicity of hematogenously distributed LS180 cells. Kim et al., *Proc. Natl. Acad. Sci. USA*, 95: 9325-9330, 1998. FIG. 7 shows that metastatic lung tumor formation is inhibited by treatment with AcGnG-NM. LS180 cells were grown with or without 50 µM AcGnG-NM for 6 days. To test if altering carbohydrate ligands on the tumor cells had a similar effect, SCID mice were injected with normal or disaccharide-treated LS180 cells via the tail vein. After 4 weeks, the animals were sacrificed and formation of lung tumor foci was assessed at necropsy by counting nodules on the lung surface and in histologic sections. Numerous foci were present on lungs from animals injected with untreated cells, whereas foci were less numerous in animals receiving disaccharide-treated cells (n=8, p<0.0002, Student's t-test. See FIG. 7C. A similar trend was noted on examination of foci in histologic sections (p<0.02). No foci were found in other organs by surface- and histologic surveys. A human metastatic lung adenocarcinoma cell line (HAL8) was also examined. These cells behaved similarly, although the absolute number of tumor foci was much lower.

Cytolysis of tumor cells is affected by altered platelet protection. Altered platelet adhesion following AcGnG-NM treatment of tumor cells may play an important mechanistic role in the in vivo findings reported above, possibly by protecting tumor cells from immune-mediated lysis. Borsig et al., *Proc. Natl. Acad. Sci. USA*, 98: 3352-3357, 2001; Nieswandt et al., *Cancer Res.*, 59: 1295-1300, 1999; Mannel et al., *Mol Pathol.*, 50: 175-185, 1997. See FIG. 5. To examine this possibility, LS180 tumor cells were loaded with $^{51}$Cr and mixed with varying numbers of cytolytic immune effector cells. See FIG. 8. The extent of cell lysis was proportional to the ratio of effector to target (E:T). Adding platelets to the incubation significantly reduced cytolysis, although some lysis was noted at very high E:T values outside the range of values that would occur in a typical experimental metastasis assay performed in mice (indicated by the broken vertical lines in FIG. 8). P-selectin deficient platelets showed a marked reduction in their ability to protect tumor cells over the same range. Platelet protection was also markedly reduced following treatment of the tumor cells with AcGnG-NM. Exposure of disaccharide-treated and untreated LS180 cells to whole human blood gave comparable results (FIG. 8, inset), although the overall effect and extent of lysis was significantly greater. Together, these findings demonstrate that P-selectin on platelets binding to sLe$^x$ determinants on tumor cells provides protection against leukocyte-mediated cytolysis. Moreover, they show that treatment with AcGnG-NM inhibits platelet-mediated protection of the cells. Vertical dashed lines represent an estimate of the range of E:T ratios (peripheral-blood mononuclear cells to tumor cells) that occur in vivo during biodistribution experiments. Open circles, no platelets were added; filled triangles, P-selectin positive platelets were added; open triangles, P-selectin-negative platelets were added; filled squares, tumor cells were treated with peracetylated GnG-NM and mixed with P-selectin-positive platelets. The experiment was performed in triplicate, and average values+/−standard deviations are shown.

Example 6

Acetylated Disaccharides Inhibit Metastatic Potential of Human Adenocarcinoma Cells In Vivo Compounds and methods for treatment or prevention of neoplastic disease or metastatic disease utilize a class of chemotherapeutic agents comprising acetylated disaccharides. Experiments showed that treatment of human adenocarcinoma cells with a disaccharide-based primer of sLe$^x$, e.g., acetylated disaccharides, can markedly inhibit their metastatic potential in vivo. Mechanistically, the compound appears to work by (i) priming the synthesis of oligosaccharides related to Lewis antigens, (ii) blocking the function of sLe$^x$ on cell surface glycoconjugates, and (iii) inhibiting selectin-dependent events that promote hematogenous metastasis, including platelet adhesion and attachment to endothelial cells. Platelet adhesion appears to confer protection from immune cytolytic responses. The findings complement recent studies in mice that showed a profound effect of altering host selectin expression on the metastatic potential of tumor cells in the circulation. Biancone et al., *J. Exp. Med.*, 183: 581-587, 1996; Frenette et al., *Thromb Haemost*, 78: 60-64, 1997; Kim et al., *Proc. Natl. Acad. Sci. USA*, 95: 9325-9330, 1998; Borsig et al., *Proc. Natl. Acad. Sci. USA*, 98: 3352-3357, 2001. Loss of tumor-cell sLe$^x$ also resulted in a concomitant and equally potent reduction in interactions with E-selectin in vitro, which may significantly interfere with adhesion to activated endothelia. One might predict that L-selectin ligands expressed on tumor cells would also be affected, which would prevent leukocyte interactions that facilitate tumor growth. Borsig et al., *Proc. Natl. Acad. Sci. USA*, 99: 2193-2198, 2002. Together, these findings imply that AcGnG-NM and related compounds may inhibit multiple interactions between tumor cells and selectin-bearing host elements (platelets, endothelia, and leukocytes) during hematogenous metastasis.

Figure 8:
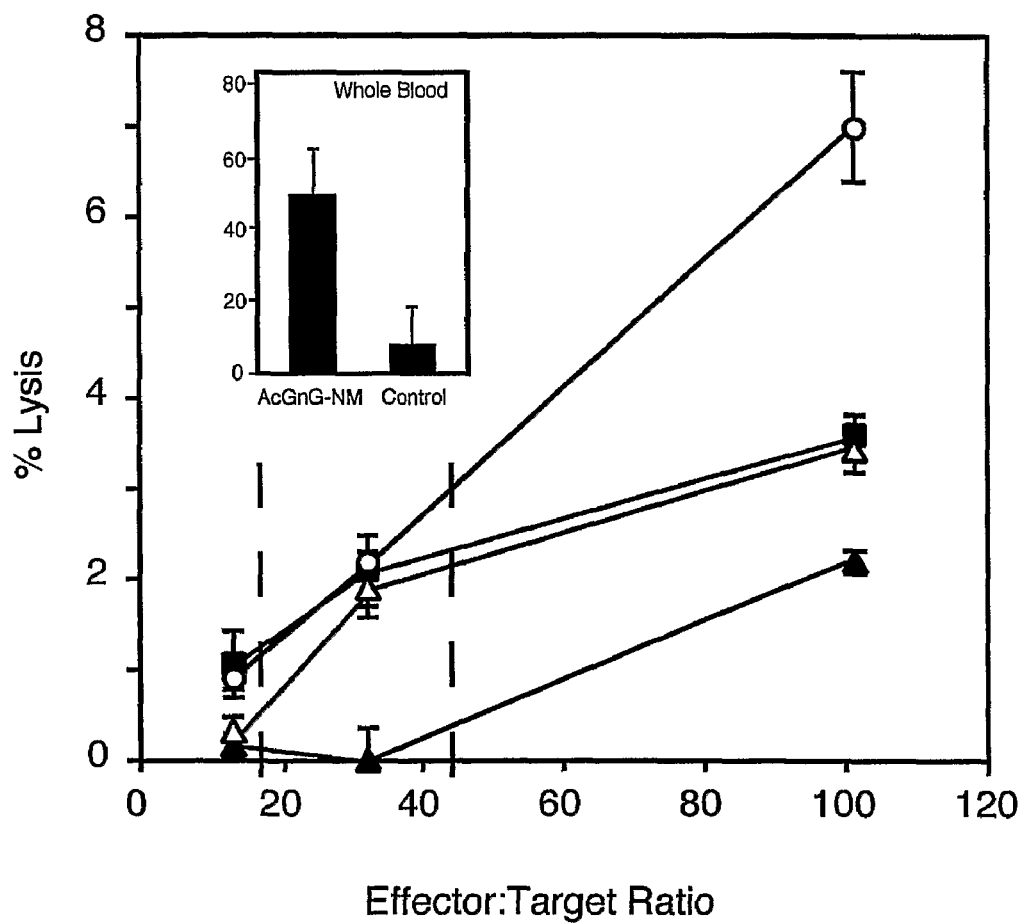
FIG. 8. Cytolysis in the presence of platelets is reduced following treatment of tumor cells with AcGnG-NM.

The treatment of tumor cells with AcGnG-NM has a particularly important effect on metastatic potential as a result of altered platelet adhesion. As shown in FIG. 8, selectin-mediated platelet adhesion endows tumor cells with significant protection from immune-mediated cytolysis, which may explain the higher tumorigenicity of untreated cells compared to cells treated with the disaccharide inhibitor (FIG. 7). Since these experiments were performed in SCID mice, humoral factors and T-cell mediated responses should not be involved, but elements of innate immunity (e.g. innate cytotoxic responses, NK cells, and the like.) may play a role. Ohyama et al., *Proc. Natl. Acad. Sci. USA*, 99: 13789-13794, 2002. The apparent protection of tumor cells by platelets critically depends on P-selectin-carbohydrate interactions since P-selectin deficiency dampens the effect both in vivo and in vitro. Upon injection of treated cells, sLe$^x$ begins to reappear on the cell surface with a $t_{1/2}$ of ~6 hr. This suggests that cytolysis occurs relatively rapidly and that interfering with platelet adhesion to tumor cells soon after their release into the circulation will render the cells more sensitive to killing. Other inhibitory agents, such as heparin or mucin fragments, also transiently block selectin dependent adhesion and block tumor formation. Borsig et al., *Proc. Natl. Acad. Sci. USA*, 98: 3352-3357, 2001. These agents are rapidly cleared from the circulation, but nevertheless have profound effects on ultimate colonization of the lungs by metastatic cells. Thus, antimetastatic agents that target selectin-carbohydrate interactions need only to act in a narrow time frame to be effective.

A final consideration is the ability of selectins to participate in "arresting" newly circulating tumor cells in organ capillary beds. Entrapment of emboli may have important consequences on the eventual uptake and growth of tumor "seeds" into large metastatic tumor foci. AcGnG-NM treated LS180 cells showed a limited ability to eventually grow as tumors in the lungs of immunodeficient mice harboring the cells for a 4-week period after tail-vein delivery (FIG. 7). While alterations in tumor sLe$^x$ may have an as-yet unexplained effect on tumor growth (including apoptosis), an initial inhibition of selectin-mediated capillary arrest may be critical to the survival of metastases. Additional evidence supporting this view includes: (i) Treatment of adenocarcinoma cells with AcGnG-NM (up to 50 μM) has minimal effects on LS180 growth in culture; (ii) experimental mice were not maintained on pharmacologic AcGnG-NM after tumor cell injection, indicating that the effects are rapid and independent of continuous inhibition; and (iii) while tumors that grew in experimental mice were markedly fewer in number, tumor size in the two groups was approximately the same. A recent study highlights the importance of an early period of intravascular tumor residence and proliferation before extravasation and uptake. Al-Mehdi et al., *Nat. Med.,* 6: 100-102, 2000. The probability of securing a prolonged intravascular period of arrest should increase following selectin-mediated formation of platelet-tumor emboli and direct contact of tumor cells with endothelial selecting. Inhibition of sLe$^X$ mediated adhesion would be expected to decrease these parameters. A recent study demonstrates that inhibition of β3 integrins also interferes with hematogenous metastasis in a platelet dependent fashion, consistent with this idea. Trikha et al., *Cancer Res.,* 62: 2824-2833, 2002. These findings imply a potential role for AcGnG-NM or related compounds as possible anti-metastasis agents for treating human cancer.

Example 7

Figure 9:
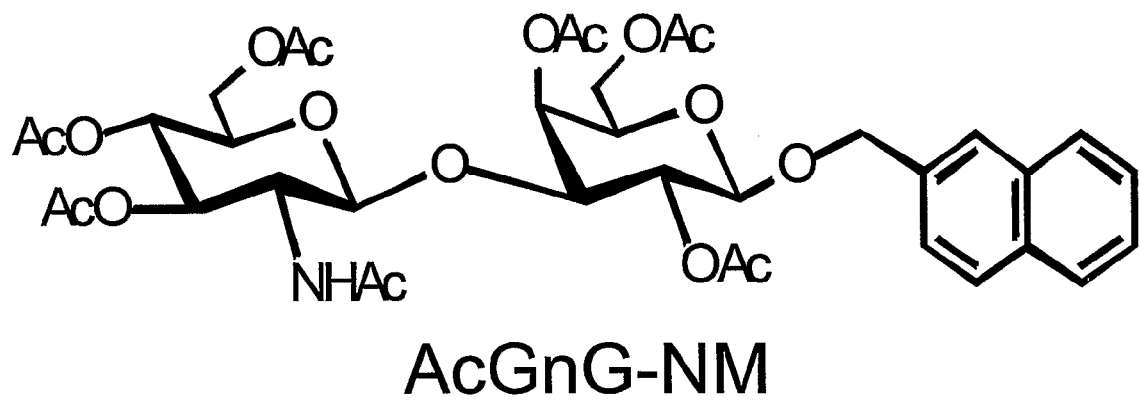
FIG. 9. Chemical structure of synthetic disaccharide decoy.

Synthetic Acetylated Disaccharide Decoy Compositions as an Anti-Metastasis Agents A synthetic disaccharide decoy, peracetylated GlcNAcβ1,3Galβ-O-naphthalenemethanol (GlcNAcβ3Gal-NM) was prepared as described (Sarkar et al., 1997; Blixt et al., 2001). The structure of GlcNAcβ3Gal-NM is shown in FIG. 9.

The general structure of acetylated disaccharides of the present invention include, but are not limited to, per-O-acetylated GlcNAcβ1,3Galβ-O-naphthalenemethanol (GlcNAcβ1,3Gal-NM); per-O-acetylated Galβ1,4GlcNAc-X—R; per-O-acetylated Galβ1,3GlcNAc-X—R; per-O-acetylated Galβ1,3GalNAc-X—R; per-O-acetylated GlcNAcβ1,3Gal-X—R; per-O-acetylated GlcNAcβ1,3GalNAc-X—R; per-O-acetylated GlcNAcβ1,6GalNAc-X—R; per-O-acetylated GlcNAcβ1,4GlcNAc-X—R; wherein R is an aglycone, including but not limited to benzyl, phenyl, naphthol, naphthalenemethanol, indenol, a heterocyclic derivative of indenol, a heterocyclic derivative of naphthol, a heterocyclic derivative of naphthalenemethanol, an alkyl group of 1-16 carbons, or a polyisoprenoid.

Table 3 shows exemplary and additional analog structures of synthetic acetylated disaccharide decoys, that have been shown to be active in in vitro cell based assays.

TABLE 3

Synthetic Acetylated Disaccharide Compositions per-O-acetylated Galβ1,4GlcNAc-O-NM
per-O-acetylated GlcNAcβ1,3Gal-O-NM
per-O-acetylated GlcNAcβ1,3Gal-O-Bn
per-O-acetylated GlcNAcβ1,3Gal-O-Ph
per-O-acetylated GlcNAcβ1,3Gal-O-2-naphthol
per-O-acetylated Galβ1,3GalNAc-O-NM
per-O-acetylated GlcNAcβ1,3GalNAc-O-NM
per-O-acetylated GlcNAcβ1,6GalNAc-O-NM
per-O-acetylated 3-deoxy-GlcNAcβ1,3Gal-O-NM
per-O-acetylated 4-deoxy-GlcNAcβ1,3Gal-O-NM
per-O-acetylated 3-fluoro-GlcNAcβ1,3Gal-O-NM
per-O-acetylated 4-fluoro-GlcNAcβ1,3Gal-O-NM
per-O-acetylated Galβ1,4(3-methoxy)-GlcNAc-O-NM
per-O-acetylated 3-methoxy-GlcNAcβ1,3Gal-O-Bn
per-O-acetylated 4-methoxy-GlcNAcβ1,3Gal-O-Bn Example 8

In Vitro Characterization of LLC Cells after Disaccharide Treatment

LLC cells were treated in culture for 4 days in the absence or presence of 50 μM peracetylated GlcNAcβ3Gal-NM. See FIG. 10A. To quantitate sLex on the surface of LLC cells monoclonal antibody, CSLEX-1 binding to the cells was measured as described (Brown et al, *J. Biol. Chem.* 278: 23352-23359, 2003). The data show that treatment of the cells with the compound reduces sLex expression. See FIG. 10B. Flow cytometry measures cell surface carbohydrate structures (Koenig et al, 1998). AAL and MAH are plant lectins. PsIg is a mouse selectin chimera Treatment of LLC cells with the disaccharide reduces AAL reactivity (decrease in fucose) but has no effect on sialylation (MAH). Treatment with sialidase abolishes PsIg binding. sialyltransferase and fucosyltransferase enzyme assays. See FIG. 10C. LLC cells have higher sialyltransferase activity than fucosyltransferase activity. It was found that the compounds of the present invention generally inhibit sLex formation by blocking the pathway with the least activity, in this case fucosylation.

Example 9

Altered Adhesion of Disaccharide Treated Cells to Immobilized P-Selectin

Figure 11:
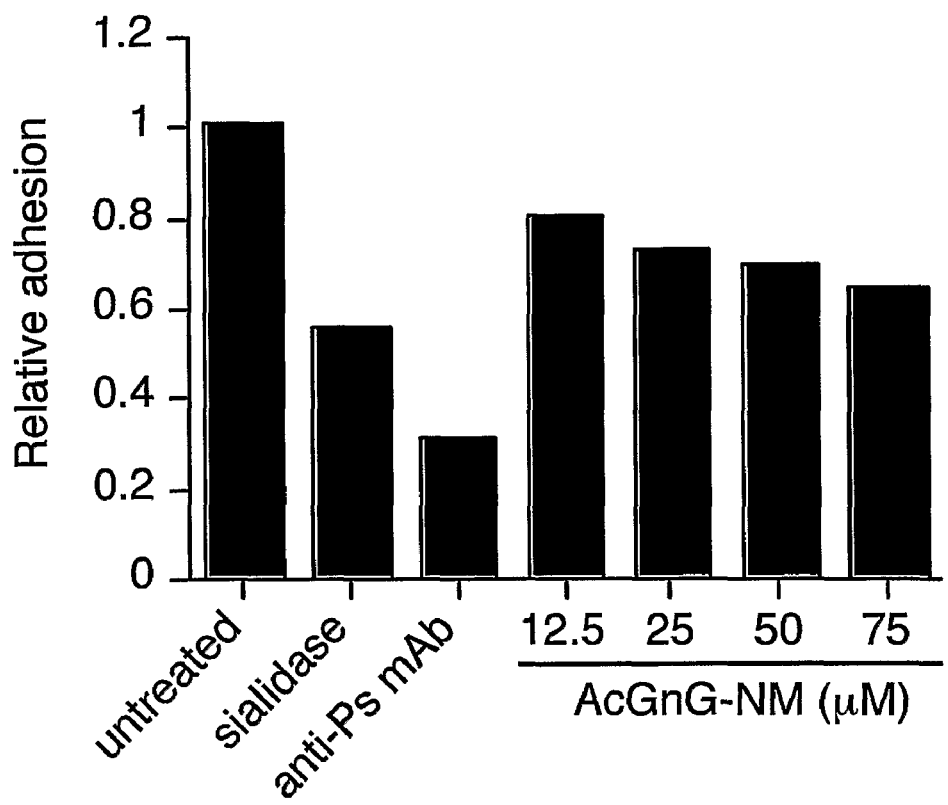
FIG. 11. Altered adhesion of disaccharide treated cells to immobilized P-selectin.

LLC cells were "panned" onto wells precoated with recombinant P-selectin (R&D Systems, Minneapolis, M) as described (Brown et al., 2003; Fuster et al., *Cancer Research* 63: 2775-2781, 2003). See FIG. 11. The extent of adhesion was normalized to the value obtained for cells not treated with disaccharide. Controls included sialidase and anti-Ps monoclonal antibody treatment. Disaccharide treatment caused a moderate reduction in cell adhesion treatment.

Example 10

Figure 12:
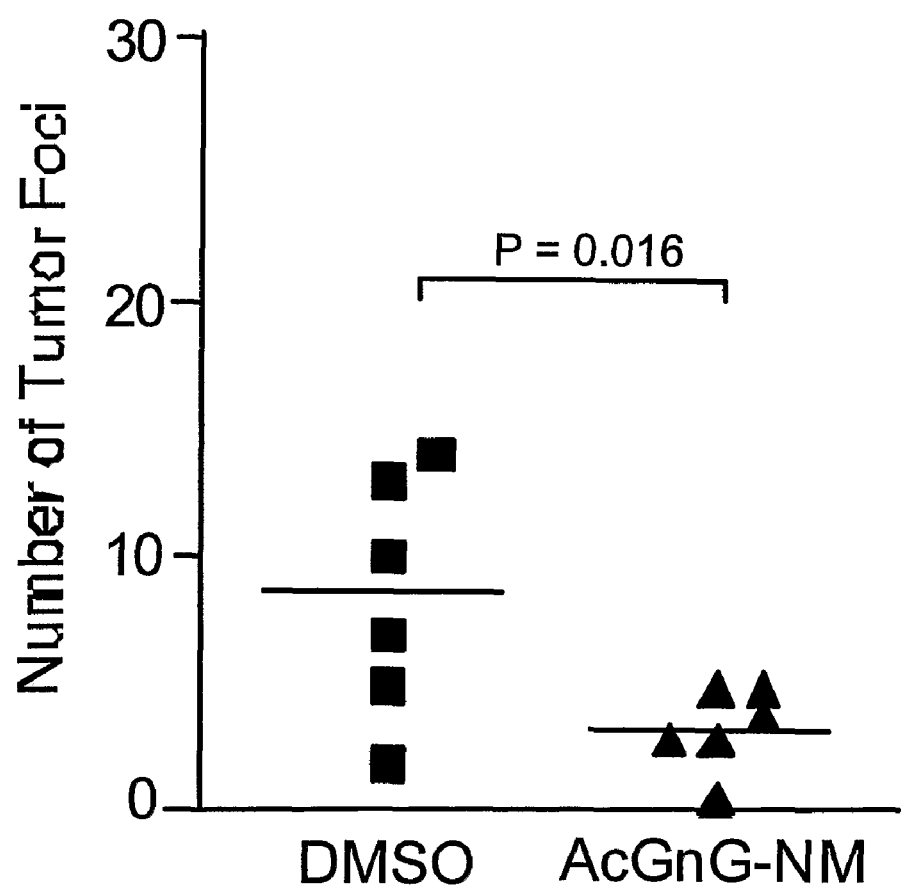
FIG. 12. Peracetylated GlcNAcβ3Gal-NM inhibits experimental metastasis.

Peracetylated GlcNAcβ3Gal-NM Inhibits Experimental Metastasis (A) LLC cells were treated in culture for 4 days with peracetylated GlcNAcβ3Gal-NM or vehicle (DMSO/propylene glycol, v/v 1:1). See FIG. 12. Single-cell suspensions ($2 \times 10^5$) were injected in the tail-veins of Es1(e) mice. After 3 weeks, the mice were sacrificed and the number of tumors present on the surface of the lungs was determined by visual inspection. Injection of disaccharide-treated cells resulted in significantly fewer tumor foci.

Example 11

Peracetylated GlcNAcβ3Gal-NM Inhibits Spontaneous Tumor Metastasis

Osmotic pumps (ref 4) containing vehicle or peracetylated GlcNAcβ3Gal-NM were surgically implanted in a dorsal skin fold of Es1(e) mice and LLC cells ($5 \times 10^5$) were implanted subcutaneously in the hindquarter. See FIG. 13. The dose rate of compound was ~1 mg/day/mouse. Panel A. To detect tumor cells in the lungs, after 4 weeks each animal was injected intraperitoneally with 1 mg of BrdU (bromodeoxyuridine (BrdU), which is taken up by dividing cells—tumor cells, and therefore indicates the quantity of tumor cells in the lungs when cells from the lungs are stained with anti-BrdU antibodies). The animals were sacrificed, the heart was perfused with PBS and the lungs removed. Each lung was incubated with collagenase (10 mg/ml, 1 h, 37° C.), syringed through an 18-gauge needle and filtered through a 40 μl pore nylon filter, and cells were fixed (70% ethanol, $1 \times 10^6$ cells/ml). The relative number of BrdU-labeled cells in the lungs was determined by flow cytometry (FACS) using a mouse anti-BrdU-FITC antibody. Control experiments used mouse IgG-FITC antibody. Statistics were calculated by one-way ANOVA tests comparing three groups of 4-7 animals. In panel B, the experiment was done exactly as in panel A, except one set of animals were dosed with inactive peracetylated disaccharide Galβ3Gal-NM. Statistics were calculated by student t-test comparing two groups of 4-7 animals.

Example 12

P-Sel$^{-/-}$ Phenocopies AcGnG-NM Treatment in Mice

Figure 14:
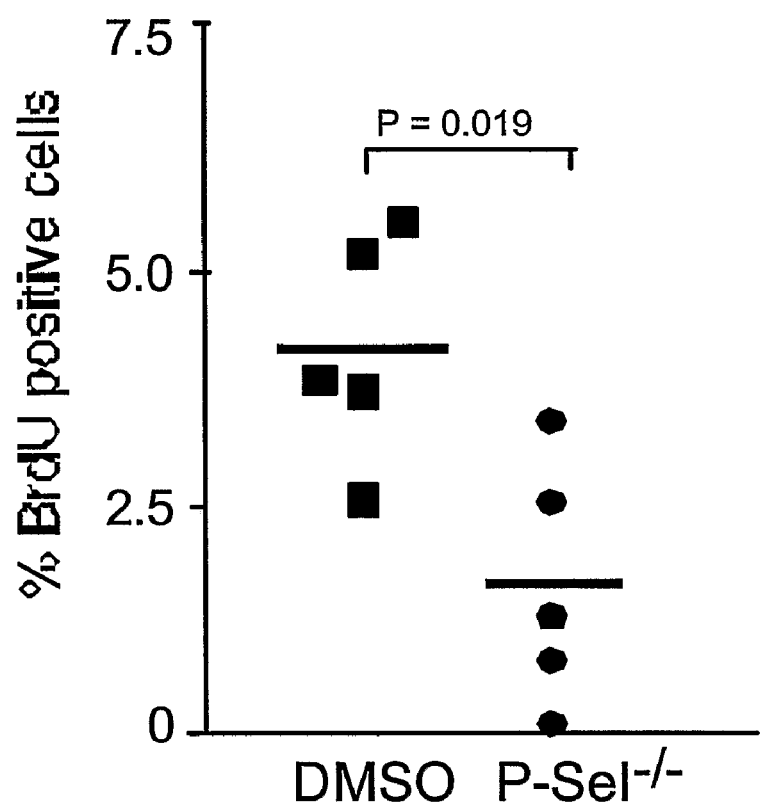
FIG. 14. P-Sel$^{-/-}$ phenocopies AcGnG-NM treatment in mice.

LLC cells ($6 \times 10^5$) were implanted subcutaneously in the hindquarter of P-sel$^{-/-}$ mice. See FIG. 14. To detect tumor cells in the lungs, after 4 weeks, each animal was injected intraperitoneally with 1 mg of BrdU. The animals were sacrificed, heart perfused with PBS and the lungs removed. The relative number of BrdU-labeled cells in the lungs was determined as described in FIG. 5. Statistics were calculated by student t-test comparing two groups of 4-7 animals.

Example 13

Blood Cell Counts are Unaffected by Treatment with AcGlcNAcβ3Gal-NM

Table 4 shows that levels of blood cell components are not affected by in vitro treatment with the compound, AcGlcNAcβ3Gal-NM. These results show a lack of toxicity and indicate that the compound acts directly on the tumor cells. The compounds had no effect in experiments measuring neutrophil recruitment after inducing peritonitis.

TABLE 4

| | Blood cell counts | | |
|---|---|---|---|
| Cell Type | Untreated (n = 375) | Vehicle treated (n = 15) | AcGlcNAcβ3Gal-NM treated (n = 13) |
| Total Leukocytes (K/μL) | 6.5 ± 2.8 | 7.9 ± 1.6 | 7.8 ± 2.6 |
| Neutrophils (K/μL) | 1.1 ± 0.7 | 1.9 ± 1.0 | 1.5 ± 0.5 |
| Lymphocytes (K/μL) | 5.0 ± 2.5 | 5.6 ± 0.7 | 6.1 ± 2.1 |
| Platelets (K/μL) | 961 ± 267 | 1146 ± 251 | 1031 ± 174 |
| Red Blood Cells (M/μL) | 8.64 ± 1 | 10.8 ± 1.8 | 10.5 ± 0.9 |

$K = 10^3, M = 10^6$

Example 14

Oligosaccharide Priming and Inhibition of sLe$^x$ Expression

A 4-deoxy modified acetylated disaccharide inhibits sLe$^x$ expression in the absence of oligosaccharide priming. (A) Peracetylated GlcNAcβ3Gal-NM (AcGnG-NM) stimulates the incorporation of [6-$^3$H]Gal into mixed oligosaccharides, but peracetylated 4-deoxy GlcNAcβ3Gal-NM (4-deoxy AcGnG-NM) does not. (B) Both AcGnG-NM and 4-deoxy AcGnG-NM inhibit sLe$^x$ expression in U937 cells, a monocytic leukemic cell line. See FIG. 15.

Example 15

Figure 16:
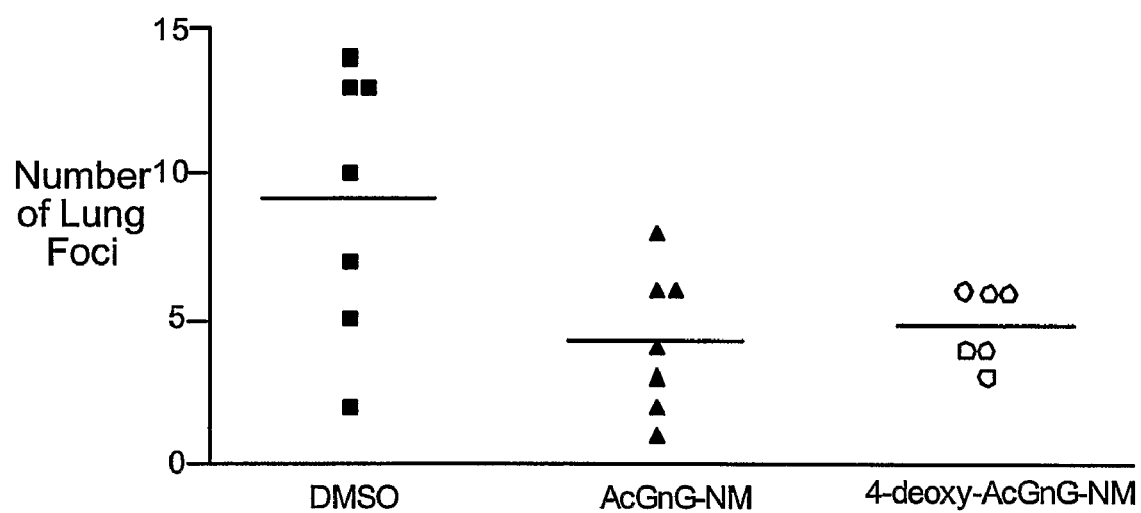
FIG. 16. Deoxy AcGnG-NM inhibits experimental metastasis of Lewis Lung Carcinoma (LLC) cells.

Deoxy AcGnG-NM Inhibits Experimental Metastasis of Lewis Lung Carcinoma (LLC) Cells LLC cells were treated in culture for 5 days with 4-deoxy AcGnG-NM, AcGnG-NM or vehicle (DMSO:propylene glycol) and then a single-cell suspension ($2 \times 10^5$ cells) was injected in the tail vein of mice. After 3 weeks, the number of tumors present on the surface of the lungs was determined. 4-deoxy AcGnG-NM inhibited experimental metastasis of LLC cells. See FIG. 16.

All publications and patent applications cited in this specification are herein incorporated by reference in their entirety for all purposes as if each individual publication or patent application were specifically and individually indicated to be incorporated by reference for all purposes.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. A method of treating disease in a mammalian subject comprising administering a therapeutically effective amount of a composition comprising a pharmaceutically-acceptable carrier and a disaccharide inhibitor of glycosyltransferase comprising the structure:

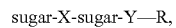

sugar-X-sugar-Y—R, wherein:
the sugars are glucose, galactose, N-acetylglucosamine, glucosamine, N-acetylgalactosamine, galactosamine, sialic acid, fucose or mannose;
X is a bridging atom, O, C, S, or N, and wherein X is a 1-2, 1-3, 1-4, or 1-6 linkage with anomeric configuration, α or β, between the sugars;
Y is a bridging atom, O, C, S, or N, with anomeric configuration, α or β;
R is a benzyl, phenyl, naphthol, naphthalenemethanol, an indenol, an alkyl group of 1-16 carbons, or a polyisoprenoid;
and wherein, independently,
the sugar is O-alkyl, O-acyl, or O-aryl substituted for a hydroxyl group;
the sugar is alkyl-, aryl-, epoxy-, amid-, thiol- or halo-substituted for a hydroxyl group; or
the sugar is S-alkyl, N-alkyl, S-acyl, N-acyl, C-acyl, S-aryl, or N-aryl substituted for a hydroxyl group;
wherein the disease is a cancer selected from the group consisting of lung cancer, breast cancer, colon cancer, gastric cancer, prostate cancer and melanoma.

2. The method of claim 1, wherein the composition is administered in a dose of from about 0.1 mg/kg to about 20 mg/kg.

3. A method for alleviating cancer in a mammalian subject comprising the step of administering to the mammalian subject a therapeutically effective dose of a composition comprising:

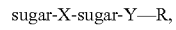

sugar-X-sugar-Y—R, or a pharmaceutically-acceptable salt or prodrug thereof;

wherein:
the sugars are glucose, galactose, N-acetylglucosamine, glucosamine, N-acetylgalactosamine, galactosamine, sialic acid, fucose or mannose;
X is a bridging atom, O, C, S, or N, and wherein X is a 1-2, 1-3, 1-4, or 1-6 linkage with anomeric configuration, α or β, between the sugars;
Y is a bridging atom, O, C, S, or N, with anomeric configuration, α or β;
R is a benzyl, phenyl, naphthol, naphthalenemethanol, an indenol, an alkyl group of 1-16 carbons, or a polyisoprenoid;
and wherein, independently,
the sugar is O-alkyl, O-acyl, or O-aryl substituted for a hydroxyl group;
the sugar is alkyl-, aryl-, epoxy-, amid-, thiol- or halo- substituted for a hydroxyl group; or
the sugar is S-alkyl, N-alkyl, S-acyl, N-acyl, C-acyl, S-aryl, or N-aryl substituted for a hydroxyl group;
and wherein the cancer is selected from the group consisting of lung cancer, breast cancer, colon cancer, gastric cancer, prostate cancer and melanoma, and the cancer in the mammalian subject is alleviated.

4. The method of claim 3 wherein the cancer is an adenocarcinoma.

5. The method of claim 3 wherein the cancer is metastatic cancer.

6. The method of claim 3, wherein the composition is administered in a dose of from about 0.1 mg/kg to about 20 mg/kg.

7. A method for the inhibiting tumor metastasis in a mammalian subject having cancer, the method comprising administration of a therapeutically effective dose of a composition comprising:

sugar-X-sugar-Y—R, wherein:
the sugars are glucose, galactose, N-acetylglucosamine, glucosamine, N-acetylgalactosamine, galactosamine, sialic acid, fucose or mannose;
X is a bridging atom, O, C, S, or N, and wherein X is a 1-2, 1-3, 1-4, or 1-6 linkage with anomeric configuration, α or β, between the sugars;
Y is a bridging atom, O, C, S, or N, with anomeric configuration, α or β;
R is a benzyl, phenyl, naphthol, naphthalenemethanol, an indenol, an alkyl group of 1-16 carbons, or a polyisoprenoid;
and wherein, independently,
the sugar is O-alkyl, O-acyl, or O-aryl substituted for a hydroxyl group;
the sugar is alkyl-, aryl-, epoxy-, amid-, thiol- or halo- substituted for a hydroxyl group; or
the sugar is S-alkyl, N-alkyl, S-acyl, N-acyl, C-acyl, S-aryl, or N-aryl substituted for a hydroxyl group;
wherein the cancer is selected from the group consisting of lung cancer, breast cancer, colon cancer, gastric cancer, prostate cancer and melanoma.

8. The method of claim 7, wherein the disaccharide is per-O-acetylated Galβ1,4GlcNAc-Y—R, per-O-acetylated Galβ1,3GlcNAc-Y—R, per-O-acetylated Galβ1,3GalNAc-Y—R, per-O-acetylated GlcNAcβ1,3Gal-Y—R, per-O-acetylated GlcNAcβ1,3GalNAc-Y—R, per-O-acetylated GlcNAcβ1,6GalNAc-Y—R, or per-O-acetylated GlcNAcβ1,4GlcNAc-Y—R, R is a benzyl, phenyl, naphthol, naphthalenemethanol, indenol, an alkyl group of 1-16 carbons, or a polyisoprenoid.

9. The method of claim 7, wherein the disaccharide is per-O-acetylated Galβ1,4GlcNAc-O-2-naphthalenemethanol (NM), per-O-acetylated GlcNAcβ1,3Gal-O-NM, per-O-acetylated GlcNAcβ1,3Gal-O-Bn, per-O-acetylated GlcNAcβ1,3Gal-O-Ph, per-O-acetylated GlcNAcβ1,3Gal-O-2-naphthol, per-O-acetylated Galβ1,3GalNAc-O-NM, per-O-acetylated GlcNAcβ1,3GalNAc-O-NM, per-O-acetylated GlcNAcβ1,6GalNAc-O-NM, per-O-acetylated 3-deoxy-GlcNAcβ1,3Gal-O-NM, per-O-acetylated 4-deoxy-GlcNAcβ1,3Gal-O-NM, per-O-acetylated 3-fluoro-GlcNAcβ1,3Gal-O-NM, per-O-acetylated 4-fluoro-GlcNAcβ1,3Gal-O-NM, per-O-acetylated Galβ1,4(3-methoxy)-GlcNAc-O-NM, per-O-acetylated 3-methoxy-GlcNAcβ1,3Gal-O-benzyl (Bn), or per-O-acetylated 4-methoxy-GlcNAcβ1,3Gal-O-Bn.

10. The method of claim 7, wherein the disaccharide is GlcNAcβ3Galβ-O-NM; 4'-deoxy-GlcNAcβ3Gal-O-NM; 4'-fluoro-GlcNAcβ3Gal-O-NM; 4'-thio-GlcNAcβ3Gal-O-NM; 4'-methoxy-GlcNAcβ3Galβ-O-NM; 4'-amino-GlcNAclβ3Gal-O-NM; 3'-deoxy-GlcNAcβ3Galβ-O-NM; 3'-fluoro-GlcNAcβ3Gal-Oβ-NM; 3'-thio-GlcNAcβ3Gal-O-NM; 3'-methoxy-GlcNAcβ3Galβ-O-NM; 3'-amino-GlcNAcβ3Galβ-O-NM; 6'-deoxy-GlcNAcβ3Galβ-O-NM; 6'-fluoro-GlcNAcβ3Gal-Oβ-NM; 6'-thio-GlcNAcβ3Gal-O-NM; 6'-methoxy-GlcNAcβ3Galβ-O-NM; 6'-amino-GlcNAcβ3Galβ-O-NM; GlcNAcβ3Galβ-O—R, wherein R=2-naphthalenemethanol (NM), 8-methoxy-NM, 2-benzyl, phenyl, 2-naphthol, 2-naphthalenethiol, 6-hydroxyquinoline, 5-hydroxyindole, cis/trans-decahydro-2-naphthol, or 2-[oxyethylene]$_n$-2-naphthol; GlcN[$^3$H]Acβ3Galβ-O-NM; or GlcNAcβ3Galβ-O—[$^3$H]NM.

11. A method for regulating biosynthesis of a naturally occurring polysaccharide in a cell, comprising the step of contacting the cell with a pharmacologically effective amount of a composition comprising:

sugar-X-sugar-Y—R, wherein:
the sugars are glucose, galactose, N-acetylglucosamine, glucosamine, N-acetylgalactosamine, galactosamine, sialic acid, fucose or mannose;
X is a bridging atom, O, C, S, or N, and wherein X is a 1-2, 1-3, 1-4, or 1-6 linkage with anomeric configuration, α or β, between the sugars;
Y is a bridging atom, O, C, S, or N, with anomeric configuration, α or β;
R is a benzyl, phenyl, naphthol, naphthalenemethanol, an indenol, an alkyl group of 1-16 carbons, or a polyisoprenoid,
and wherein, independently,
the sugar is O-alkyl, O-acyl, or O-aryl substituted for a hydroxyl group;
the sugar is alkyl-, aryl-, epoxy-, amid-, thiol- or halo- substituted for a hydroxyl group;
the sugar is O-acyl, S-acyl, N-acyl or C-acyl substituted for a hydroxyl group; or
the sugar is O-aryl, S-aryl, or N-aryl substituted for a hydroxyl group,
wherein the cell is a lung cancer cell, a breast cancer cell, a colon cancer cell, a gastric cancer cell, a prostate cancer cell, or a melanoma cell.

12. A method for alleviating cancer in a mammal believed to be responsive to treatment with a compound that blocks expression of carbohydrate antigens on a surface of a cell, comprising administering to the mammal a therapeutically effective dose of a compound comprising:

sugar-X-sugar-Y—R, or a pharmaceutically-acceptable salt or prodrug thereof;
wherein:
the sugars are glucose, galactose, N-acetylglucosamine, glucosamine, N-acetylgalactosamine, galactosamine, sialic acid, fucose or mannose;
X is a bridging atom, O, C, S, or N, and wherein X is a 1-2, 1-3, 1-4, or 1-6 linkage with anomeric configuration, α or β, between the sugars;
Y is a bridging atom, O, C, S, or N, with anomeric configuration, α or β;
R is a benzyl, phenyl, naphthol, naphthalenemethanol, an indenol, an alkyl group of 1-16 carbons, or a polyisoprenoid;
and wherein, independently,
the sugar is O-alkyl, O-acyl, or O-aryl substituted for a hydroxyl group;
the sugar is alkyl-, aryl-, epoxy-, amid-, thiol- or halo-substituted for a hydroxyl group; or
the sugar is S-alkyl, N-alkyl, S-acyl, N-acyl, C-acyl, S-aryl, or N-aryl substituted for a hydroxyl group;
wherein the cancer is selected from the group consisting of lung cancer, breast cancer, colon cancer, gastric cancer, prostate cancer and melanoma.

13. The method of claim 12 wherein the carbohydrate antigen is a ligand for a cell surface receptor.

14. The method of claim 13 wherein the carbohydrate antigen is a Lewis carbohydrate antigen.

15. The method of claim 14 wherein the Lewis carbohydrate antigen is a sialyl (sLe$^x$) carbohydrate or a sialyl (sLe$^a$) carbohydrate.

16. The method of claim 13 wherein the carbohydrate antigen is a ligand for a selectin.

17. The method of claim 16 wherein the selectin is an E-selectin, P-selectin, or L-selectin.

18. The method of claim 12 wherein the cancer is metastatic cancer.

19. The method of claim 1, wherein the disaccharide is per-O-acetylated Galβ1,4GlcNAc-Y—R, per-O-acetylated Galβ1,3GlcNAc-Y—R, per-O-acetylated Galβ1,3GalNAc-Y—R, per-O-acetylated GlcNAcβ1,3Gal-Y—R, per-O-acetylated GlcNAcβ1,3GalNAc-Y—R, per-O-acetylated GlcNAcβ1,6GalNAc-Y—R, or per-O-acetylated GlcNAcβ1,4GlcNAc-Y—R, R is a benzyl, phenyl, naphthol, naphthalenemethanol, an indenol, an alkyl group of 1-16 carbons, or a polyisoprenoid.

20. The method of claim 1, wherein the disaccharide is per-O-acetylated Galβ1,4GlcNAc-O-2-naphthalenemethanol (NM), per-O-acetylated GlcNAcβ1,3Gal-O-NM, per-O-acetylated GlcNAcβ1,3Gal-O-Bn, per-O-acetylated GlcNAcβ1,3Gal-O-Ph, per-O-acetylated GlcNAcβ1,3Gal-O-2-naphthol, per-O-acetylated Galβ1,3GalNAc-O-NM, per-O-acetylated GlcNAcβ1,3GalNAc-O-NM, per-O-acetylated GlcNAcβ1,6GalNAc-O-NM, per-O-acetylated 3-deoxy-GlcNAcβ1,3Gal-O-NM, per-O-acetylated 4-deoxy-GlcNAcβ1,3Gal-O-NM, per-O-acetylated 3-fluoro-GlcNAcβ1,3Gal-O-NM, per-O-acetylated 4-fluoro-GlcNAcβ1,3Gal-O-NM, per-O-acetylated Galβ1,4(3-methoxy)-GlcNAc-O-NM, per-O-acetylated 3-methoxy-GlcNAcβ1,3Gal-O-benzyl (Bn), or per-O-acetylated 4-methoxy-GlcNAcβ1,3Gal-O-Bn.

21. The method of claim 1, wherein the disaccharide is GlcNAcβ3Galβ-O-NM; 4'-deoxy-GlcNAcβ3Gal-O-NM; 4'-fluoro-GlcNAcβ3Gal-O-NM; 4'-thio-GlcNAcβ3Gal-O-NM; 4'-methoxy-GlcNAcβ3Galβ-O-NM; 4'-amino-GlcNAcβ3Gal-O-NM; 3'-deoxy-GlcNAcβ3Galβ-O-NM; 3'-fluoro-GlcNAcβ3Gal-Oβ-NM; 3'-thio-GlcNAcβ3Gal-O-NM; 3'-methoxy-GlcNAcβ3Galβ-O-NM; 3'-amino-GlcNAcβ3Galβ-O-NM; 6'-deoxy-GlcNAcβ3Galβ-O-NM; 6'-fluoro-GlcNAcβ3Gal-Oβ-NM; 6'-thio-GlcNAcβ3Gal-O-NM; 6'-methoxy-GlcNAcβ3Galβ-O-NM; 6'-amino-GlcNAcβ3Galβ-O-NM; GlcNAcβ3Galβ-O—R, wherein R=2-naphthalenemethanol (NM), 8-methoxy-NM, 2-benzyl, phenyl, 2-naphthol, 2-naphthalenethiol, 6-hydroxyquinoline, 5-hydroxyindole, cis/trans-decahydro-2-naphthol, or 2-[oxyethylene]$_n$-2-naphthol; GlcN[$^3$H]Acβ3Galβ-O-NM; or GlcNAcβ3Galβ-O—[$^3$H]NM.

22. The method of claim 1 wherein the cancer is metastatic cancer.

23. The method of claim 3, wherein the disaccharide is per-O-acetylated Galβ1,4GlcNAc-Y—R, per-O-acetylated Galβ1,3GlcNAc-Y—R, per-O-acetylated Galβ1,3GalNAc-Y—R, per-O-acetylated GlcNAcβ1,3Gal-Y—R, per-O-acetylated GlcNAcβ1,3GalNAc-Y—R, per-O-acetylated GlcNAcβ1,6GalNAc-Y—R, or per-O-acetylated GlcNAcβ1,4GlcNAc-Y—R, R is a benzyl, phenyl, naphthol, naphthalenemethanol, an indenol, an alkyl group of 1-16 carbons, or a polyisoprenoid.

24. The method of claim 3, wherein the disaccharide is per-O-acetylated Galβ1,4GlcNAc-O-2-naphthalenemethanol (NM), per-O-acetylated GlcNAcβ1,3Gal-O-NM, per-O-acetylated GlcNAcβ1,3Gal-O-Bn, per-O-acetylated GlcNAcβ1,3Gal-O-Ph, per-O-acetylated GlcNAcβ1,3Gal-O-2-naphthol, per-O-acetylated Galβ1,3GalNAc-O-NM, per-O-acetylated GlcNAcβ1,3GalNAc-O-NM, per-O-acetylated GlcNAcβ1,6GalNAc-O-NM, per-O-acetylated 3-deoxy-GlcNAcβ1,3Gal-O-NM, per-O-acetylated 4-deoxy-GlcNAcβ1,3Gal-O-NM, per-O-acetylated 3-fluoro-GlcNAcβ1,3Gal-O-NM, per-O-acetylated 4-fluoro-GlcNAcβ1,3Gal-O-NM, per-O-acetylated Galβ1,4(3-methoxy)-GlcNAc-O-NM, per-O-acetylated 3-methoxy-GlcNAcβ1,3Gal-O-benzyl (Bn), or per-O-acetylated 4-methoxy-GlcNAcβ1,3Gal-O-Bn.

25. The method of claim 3, wherein the disaccharide is GlcNAcβ3Galβ-O-NM; 4'-deoxy-GlcNAcβ3Gal-O-NM; 4'-fluoro-GlcNAcβ3Gal-O-NM; 4'-thio-GlcNAcβ3Gal-O-NM; 4'-methoxy-GlcNAcβ3Galβ-O-NM; 4'-amino-GlcNAcβ3Gal-O-NM; 3'-deoxy-GlcNAcβ3Galβ-O-NM; 3'-fluoro-GlcNAcβ3Gal-Oβ-NM; 3'-thio-GlcNAcβ3Gal-O-NM; 3'-methoxy-GlcNAcβ3Galβ-O-NM; 3'-amino-GlcNAcβ3Galβ-O-NM; 6'-deoxy-GlcNAcβ3Galβ-O-NM; 6'-fluoro-GlcNAcβ3Gal-Oβ-NM; 6'-thio-GlcNAcβ3Gal-O-NM; 6'-methoxy-GlcNAcβ3Galβ-O-NM; 6'-amino-GlcNAcβ3Galβ-O-NM; GlcNAcβ3Galβ-O—R, wherein R=2-naphthalenemethanol (NM), 8-methoxy-NM, 2-benzyl, phenyl, 2-naphthol, 2-naphthalenethiol, 6-hydroxyquinoline, 5-hydroxyindole, cis/trans-decahydro-2-naphthol, or 2-[oxyethylene]$_n$-2-naphthol; GlcN[$^3$H]Acβ3Galβ-O-NM; or GlcNAcβ3Galβ-O—[$^3$H]NM.

26. The method of claim 7, wherein the composition is administered in a dose of from about 0.1 mg/kg to about 20 mg/kg.

27. The method of claim 11, wherein the disaccharide is per-O-acetylated Galβ1,4GlcNAc-Y—R, per-O-acetylated Galβ1,3GlcNAc-Y—R, per-O-acetylated Galβ1,3GalNAc-Y—R, per-O-acetylated GlcNAcβ1,3Gal-Y—R, per-O-acetylated GlcNAcβ1,3GalNAc-Y—R, per-O-acetylated GlcNAcβ1,6GalNAc-Y—R, or per-O-acetylated GlcNAcβ1,4GlcNAc-Y—R, R is a benzyl, phenyl, naphthol, naphthalenemethanol, an indenol, an alkyl group of 1-16 carbons, or a polyisoprenoid.

28. The method of claim 11, wherein the disaccharide is per-O-acetylated Galβ1,4GlcNAc-O-2-naphthalenemethanol (NM), per-O-acetylated GlcNAcβ1,3Gal-O-NM, per-O-acetylated GlcNAcβ1,3Gal-O-Bn, per-O-acetylated GlcNAcβ1,3Gal-O-Ph, per-O-acetylated GlcNAcβ1,3Gal-O-2-naphthol, per-O-acetylated Galβ1,3GalNAc-O-NM, per-O-acetylated GlcNAcβ1,3GalNAc-O-NM, per-O-acetylated GlcNAcβ1,6GalNAc-O-NM, per-O-acetylated 3-deoxy-GlcNAcβ1,3Gal-O-NM, per-O-acetylated 4-deoxy-GlcNAcβ1,3Gal-O-NM, per-O-acetylated 3-fluoro-GlcNAcβ1,3Gal-O-NM, per-O-acetylated 4-fluoro-GlcNAcβ1,3Gal-O-NM, per-O-acetylated Galβ1,4(3-methoxy)-GlcNAc-O-NM, per-O-acetylated 3-methoxy-GlcNAcβ1,3Gal-O-benzyl (Bn), or per-O-acetylated 4-methoxy-GlcNAcβ1,3Gal-O-Bn.

29. The method of claim 11, wherein the disaccharide is GlcNAcβ3Galβ-O-NM; 4'-deoxy-GlcNAcβ3Gal-O-NM; 4'-fluoro-GlcNAcβ3Gal-O-NM; 4'-thio-GlcNAcβ3Gal-O-NM; 4'-methoxy-GlcNAcβ3Galβ-O-NM; 4'-amino-GlcNAcβ3Gal-O-NM; 3'-deoxy-GlcNAcβ3Galβ-O-NM; 3'-fluoro-GlcNAcβ3Gal-Oβ-NM; 3'-thio-GlcNAcβ3Gal-O-NM; 3'-methoxy-GlcNAcβ3Galβ-O-NM; 3'-amino-GlcNAcβ3Galβ-O-NM; 6'-deoxy-GlcNAcβ3Galβ-O-NM; 6'-fluoro-GlcNAcβ3Gal-Oβ-NM; 6'-thio-GlcNAcβ3Gal-O-NM; 6'-methoxy-GlcNAcβ3Galβ-O-NM; 6'-amino-GlcNAcβ3Galβ-O-NM; GlcNAcβ3Galβ-O—R, wherein R=2-naphthalenemethanol (NM), 8-methoxy-NM, 2-benzyl, phenyl, 2-naphthol, 2-naphthalenethiol, 6-hydroxyquinoline, 5-hydroxyindole, cis/trans-decahydro-2-naphthol, or 2-[oxyethylene]$_n$-2-naphthol; GlcN[$^3$H]Acβ3Galβ-O-NM; or GlcNAcβ3Galβ-O—[$^3$H]NM.

30. The method of claim 12, wherein the composition is administered in a dose of from about 0.1 mg/kg to about 20 mg/kg.

31. The method of claim 12, wherein the disaccharide is per-O-acetylated Galβ1,4GlcNAc-Y—R, per-O-acetylated Galβ1,3GlcNAc-Y—R, per-O-acetylated Galβ1,3GalNAc-Y—R, per-O-acetylated GlcNAcβ1,3Gal-Y—R, per-O-acetylated GlcNAcβ1,3GalNAc-Y—R, per-O-acetylated GlcNAcβ1,6GalNAc-Y—R, or per-O-acetylated GlcNAcβ1,4GlcNAc-Y—R, R is a benzyl, phenyl, naphthol, naphthalenemethanol, an indenol, an alkyl group of 1-16 carbons, or a polyisoprenoid.

32. The method of claim 12, wherein the disaccharide is per-O-acetylated Galβ1,4GlcNAc-O-2-naphthalenemethanol (NM), per-O-acetylated GlcNAcβ1,3Gal-O-NM, per-O-acetylated GlcNAcβ1,3Gal-O-Bn, per-O-acetylated GlcNAcβ1,3Gal-O-Ph, per-O-acetylated GlcNAcβ1,3Gal-O-2-naphthol, per-O-acetylated Galβ1,3GalNAc-O-NM, per-O-acetylated GlcNAcβ1,3GalNAc-O-NM, per-O-acetylated GlcNAcβ1,6GalNAc-O-NM, per-O-acetylated 3-deoxy-GlcNAcβ1,3Gal-O-NM, per-O-acetylated 4-deoxy-GlcNAcβ1,3Gal-O-NM, per-O-acetylated 3-fluoro-GlcNAcβ1,3Gal-O-NM, per-O-acetylated 4-fluoro-GlcNAcβ1,3Gal-O-NM, per-O-acetylated Galβ1,4(3-methoxy)-GlcNAc-O-NM, per-O-acetylated 3-methoxy-GlcNAcβ1,3Gal-O-benzyl (Bn), or per-O-acetylated 4-methoxy-GlcNAcβ1,3Gal-O-Bn.

33. The method of claim 12, wherein the disaccharide is GlcNAcβ3Galβ-O-NM; 4'-deoxy-GlcNAcβ3Gal-O-NM; 4'-fluoro-GlcNAcβ3Gal-O-NM; 4'-thio-GlcNAcβ3Gal-O-NM; 4'-methoxy-GlcNAcβ3Galβ-O-NM; 4'-amino-GlcNAcβ3Gal-O-NM; 3'-deoxy-GlcNAcβ3Galβ-O-NM; 3'-fluoro-GlcNAcβ3Gal-Oβ-NM; 3'-thio-GlcNAcβ3Gal-O-NM; 3'-methoxy-GlcNAcβ3Galβ-O-NM; 3'-amino-GlcNAcβ3Galβ-O-NM; 6'-deoxy-GlcNAcβ3Galβ-O-NM; 6'-fluoro-GlcNAcβ3Gal-Oβ-NM; 6'-thio-GlcNAcβ3Gal-O-NM; 6'-methoxy-GlcNAcβ3Galβ-O-NM; 6'-amino-GlcNAcβ3Galβ-O-NM; GlcNAcβ3Galβ-O—R, wherein R=2-naphthalenemethanol (NM), 8-methoxy-NM, 2-benzyl, phenyl, 2-naphthol, 2-naphthalenethiol, 6-hydroxyquinoline, 5-hydroxyindole, cis/trans-decahydro-2-naphthol, or 2-[oxyethylene]$_n$-2-naphthol; GlcN[$^3$H]Acβ3Galβ-O-NM; or GlcNAcβ3Galβ-O—[$^3$H]NM.

\* \* \* \* \*